US011753370B2

(12) United States Patent
Wall

(10) Patent No.: US 11,753,370 B2
(45) Date of Patent: *Sep. 12, 2023

(54) METHODS OF MAKING DEUTERIUM-ENRICHED N-ACETYLCYSTEINE AMIDE (D-NACA) AND (2R, 2R')-3,3'-DISULFANEDIYL BIS(2-ACETAMIDOPROPANAMIDE) (DINACA) AND USING D-NACA AND DINACA TO TREAT DISEASES INVOLVING OXIDATIVE STRESS

(71) Applicant: Nacuity Pharmaceuticals, Inc., Fort Worth, TX (US)

(72) Inventor: G. Michael Wall, Fort Worth, TX (US)

(73) Assignee: Nacuity Pharmaceuticals, Inc., Fort Worth, TX (US)

( * ) Notice: Subject to any disclaimer, the term of this patent is extended or adjusted under 35 U.S.C. 154(b) by 5 days.

This patent is subject to a terminal disclaimer.

(21) Appl. No.: 16/928,927

(22) Filed: Jul. 14, 2020

(65) Prior Publication Data
US 2020/0385342 A1 Dec. 10, 2020

Related U.S. Application Data

(62) Division of application No. 16/180,984, filed on Nov. 5, 2018, now abandoned.

(60) Provisional application No. 62/587,246, filed on Nov. 16, 2017, provisional application No. 62/583,984, filed on Nov. 9, 2017.

(51) Int. Cl.
*C07C 323/41* (2006.01)
*C07C 319/28* (2006.01)
*A61P 27/02* (2006.01)
*A61K 9/00* (2006.01)
*A61K 9/08* (2006.01)
*C07C 319/12* (2006.01)
*C07D 277/12* (2006.01)
*C07C 319/24* (2006.01)
*A61K 31/00* (2006.01)
*A61K 31/185* (2006.01)
*A61K 47/10* (2017.01)

(52) U.S. Cl.
CPC .......... *C07C 323/41* (2013.01); *A61K 9/0048* (2013.01); *A61K 9/08* (2013.01); *A61K 31/00* (2013.01); *A61K 31/185* (2013.01); *A61K 47/10* (2013.01); *A61P 27/02* (2018.01); *C07C 319/12* (2013.01); *C07C 319/24* (2013.01); *C07C 319/28* (2013.01); *C07D 277/12* (2013.01); *C07B 2200/05* (2013.01); *C07B 2200/07* (2013.01)

(58) Field of Classification Search
CPC ....... C07C 323/41; C07C 319/28; A61P 27/02
See application file for complete search history.

(56) References Cited

U.S. PATENT DOCUMENTS

| 3,340,147 A | 9/1967 | Martin et al. |
| 5,874,468 A | 2/1999 | Atlas et al. |
| 6,420,429 B1 | 7/2002 | Atlas et al. |
| 8,354,449 B2 | 1/2013 | Goldstein |
| 8,937,099 B2 | 1/2015 | Goldstein |
| 8,993,627 B2 | 3/2015 | Goldstein |
| 9,216,162 B2 | 12/2015 | Goldstein |
| 9,763,902 B2 | 9/2017 | Warner et al. |
| 9,889,103 B2 | 2/2018 | Warner et al. |
| 10,869,846 B2 | 12/2020 | Goldstein |
| 2003/0027745 A1 | 2/2003 | Repine |
| 2005/0112572 A1 | 5/2005 | Pincemail et al. |
| 2009/0234011 A1 | 9/2009 | Goldstein |
| 2012/0142550 A1 | 6/2012 | Zehnder et al. |

(Continued)

FOREIGN PATENT DOCUMENTS

| CA | 3079196 A1 | 3/2019 |
| CA | 3078680 A1 | 5/2019 |

(Continued)

OTHER PUBLICATIONS

Campochiaro et al. Antioxid. Redox. Signal., 2015, 23, vol. 7, pp. 643-648.*
Amer, et al., "N-acetylcysteine amide (AD4) attenuates oxidative stress in beta-thalassemia blood cells." Biochimica et Biophysica Acta 1780 (2008) 249-255.
Australian Patent Office (ISA), International Search Report and Written Opinion for PCT/US2020/012968 dated Mar. 13, 2020, 10 pp.
Australian Patent Office (ISA), International Search Report and Written Opinion for PCT/US2020/012975 dated Mar. 13, 2020, 12 pp.
Australian Patent Office (ISA), International Search Report and Written Opinion for PCT/US2020/012983 dated Mar. 13, 2020, 15 pp.

(Continued)

*Primary Examiner* — Samira J Jean-Louis
(74) *Attorney, Agent, or Firm* — Edwin S. Flores; Daniel J. Chalker; Chalker Flores, LLP

(57) ABSTRACT

The present invention includes pharmaceutical composition comprising (2R,2R')-3,3'-disulfanediyl bis(2-acetamidopropanamide)(diNACA) or D₃-N-acetyl cysteine amide, or a physiologically acceptable salt thereof, having a deuterium enrichment above the natural abundance of deuterium, and derivatives or solids thereof, and methods of using diNACA to treat eye diseases and other diseases associated with oxidative damage including, e.g., antivenom, beta-thallassemia, cataract, chronic obstructive pulmonary disease, macular degeneration, contrast-induced nephropathy, asthma, lung contusion, methamphetamine-induced oxidative stress, multiple sclerosis, Parkinson's disease, platelet apoptosis, Tardive dyskinesia, Alzheimer disease, HIV-1-associated dementia, mitochondrial diseases, myocardial myopathy, neurodegenerative diseases, pulmonary fibrosis, skin pigmentation, skin in need of rejuventation, antimicrobial infection, Friedreich's ataxia.

7 Claims, 11 Drawing Sheets

(56) References Cited

U.S. PATENT DOCUMENTS

| | | |
|---|---|---|
| 2012/0150029 A1 | 6/2012 | Debuc |
| 2013/0303436 A1 | 11/2013 | Wilson |
| 2015/0164830 A1 | 6/2015 | Goldstein |
| 2017/0020914 A1 | 1/2017 | Castro Feo et al. |
| 2017/0333375 A1 | 11/2017 | Campochiaro et al. |
| 2017/0370945 A1 | 12/2017 | Campochiaro et al. |
| 2019/0135741 A1 | 5/2019 | Wall |
| 2020/0281944 A1 | 9/2020 | Piraee |

FOREIGN PATENT DOCUMENTS

| | | |
|---|---|---|
| CN | 108618993 A | 10/2018 |
| EP | 1975621 A1 | 1/2008 |
| GB | 1114369 A | 5/1968 |
| JP | 202023549 | 10/2018 |
| WO | 2003016527 | 2/2003 |
| WO | 2003016527 A2 | 2/2003 |
| WO | 2004012652 A2 | 2/2004 |
| WO | 2006/116353 A2 | 11/2006 |
| WO | 2006116353 A2 | 11/2006 |
| WO | 2010048716 A1 | 5/2010 |
| WO | 2011044230 A2 | 4/2011 |
| WO | 2013138744 A1 | 9/2013 |
| WO | 2013263545 A1 | 10/2013 |
| WO | 2014025792 A1 | 2/2014 |
| WO | 2014100361 A1 | 6/2014 |
| WO | 2015148880 A1 | 10/2015 |
| WO | 2016073829 A2 | 5/2016 |
| WO | 2016073931 A1 | 5/2016 |
| WO | 2017161318 A1 | 9/2017 |
| WO | 2019/060623 A1 | 3/2019 |
| WO | 2019060623 A1 | 3/2019 |
| WO | 2019060634 A1 | 3/2019 |
| WO | 2019060704 A1 | 3/2019 |
| WO | 2019/094383 A1 | 5/2019 |
| WO | 2019094383 A1 | 5/2019 |
| WO | 2019097434 A1 | 5/2019 |
| WO | 2019103915 A1 | 5/2019 |
| WO | 2020102810 A1 | 5/2020 |
| WO | 2020146660 A1 | 7/2020 |
| WO | 2020146666 A1 | 7/2020 |
| WO | 2020146674 A1 | 7/2020 |

OTHER PUBLICATIONS

Australian Patent Office, International Search Report and Written Opinion PCT/US2021/014819 dated Mar. 25, 2021, 18 pp.
Australian Patent Office, International Search Report and Written Opinion PCT/US2021/036210 dated Jul. 19, 2021, 12 pp.
Australian Patent Office, Examination Report for Australian Appl. No. 2020227015 dated Sep. 24, 2021, 6 pp.
Bahat-Stroomza, et al., "A novel thiol antioxidant that crosses the blood brain barrier protects dopaminergic neurons in experimental models of Parkinson"s disease. European Journal of Neuroscience, 2005; 21: 637-646.
Banerjee, et al., "HIV proteins (gp120 and Tat) and methamphetamine in oxidative stress-induced damage in the brain: Potential role of the thiol antioxidant N-acetylcysteine amide." Free Radic Biol Med. May 15, 2010; 48(10): 1388-1398.
Boone, Kevin "The K-Zone: Biophysical Data Tables", 1994-2006, downloaded from www.kevinboone.com on Mar. 14, 2009.
Carey, et al., "In vivo inhibition of l-buthionine-(S, R)-sulfoximine-induced cataracts by a novel antioxidant, N-acetylcysteine amide." Free Radical Biol Med. 2011;15.
Carey, et al. "N-acetyl-L-cysteine amide protects retinal pigment epithelium against methamphetamine-induced oxidative stress" Journal of Biophysical Chemistry, vol. 3, No. 2, 101-110 (2012).
Carroll, et al., "Simultaneous quantitation of oxidized and reduced glutathione via LC-MS/MS: An insight into the redox state of hematopoietic stem cells." Free Radical Biology and Medicine, 97 (2016) 85-94.
Celma, et al., "Determination of N-acetylcysteine in human plasma by liquid chromatography coupled to tandem mass spectrometry." J Chrom A, 870 (2000) 13-22.
Dietzsch, et al., "Cystic fibrosis: comparison of two mucolytic drugs for inhalation treatment (acetylcysteine and arginine hydrochloride)." Pediatrics 1975;55:96-100.
Dong, et al., "Compared with N-acetylcysteine (NAC), N-Acetylcysteinne Amid (NACA) Provides Increased Protein of Done Function in a Model of Retinitis Pigmentosa." Investigative Ophthalmology Visual Science, (2014), 55:1-2. (Abstract).
Ercal, et al., "Effects of a thiol antioxidant in various cataract models," Acta Ophthalmologica (2016), 94:S256 (Abstract).
Ercal, et al., High-performance liquid chromatography assay for N-acetylcysteine in biological samples following derivatization with N-(1-pyrenyl)maleimide. J Chrom B, 685 (1996) 329-334.
European Patent Office, Extended European Search Report for EP 18876329.6 dated Oct. 29, 2019.
European Patent Office, Extended European Search Report for EP 18882212.6 dated Jul. 6, 2021, 8 pp.
Giustarini, et al., Pitfalls in the analysis of the physiological antioxidant glutathione (GSH) and its disulfide (GSSG) in biological samples: an elephant in the room. J Chrom B., 1019 (2016) 21-28.
Han, et al., "Efficacy of nebulized acetylcysteine for relieving symptoms and reducing usage of expectorants in patients with radiation pneumonitis." Thoracic Cancer 2018; 1-6 doi: 10.1111/1759-7714.12938.
Intellectual Property India, First Examination Report for Indian Appl. No. 201917036550 dated Sep. 22, 2021, 7 pp.
Sokawa, et al., Analytical methods involving separation techniques for determination of low-molecular-weight biothiols in human plasma and blood. J Chrom B, 964 (2014) 103-115.
Jastrzębska, et al., "N-acetylcysteine amide (AD4) reduces cocaine-induced reinstatement." Psychopharmacology 2016;33:3437-3448.
Katz, et al., Cerebrospinal fluid concentrations of N-acetylcysteine after oral administration in Parkinsons disease. Parkinsonism and Related Disorders, 21 (2015) 500-503.
Kim, et al., "N-Acetylcysteine increases corneal cell survival in a mouse model of Fuchs endothelial corneal dystrophy," Experimental Eye Research (2014), 127:20-25.
Kusmierek, et al., Ultraviolet derivatization of low-molecular-mass thiols for high performance liquid chromatography and capillary electrophoresis analysis, J Chrom B, 879 (2011) 1290-1307.
Grinberg, et al., "N-acetylcysteine amide, a novel cell-permeating thiol, restores cellular glutathione and protects human red blood cells from oxidative stress," Free Radical Biol Med. (2005) ;38(1): 136-145.
Lee, et al., "N-Acetylcysteine Promotes Long-Term Survival of Cones in a Model of Retinitis Pigmentosa," J Cell Physiol (2011), 226:1843-1849, published online Nov. 10, 2010.
Levine, R.L., "Carbonyl modified proteins in cellular regulation, aging, and disease" Free Radic Biol Med, 2002. 32(9): p. 790-6.
Maddirala, et al. "Prevention and reversal of selenite-induced cataracts by N-acetylcysteine amide in Wistar rats" BMC Ophthalmology (2017) 17:54.
McMenamim, et al., Simultaneous analysis of multiple aminothiols in human plasma by high performance liquid chromatography with fluorescence detection, J Chrom B, 877 (2009) 3274-3281.
Miller, WF. "Aerosol therapy in acute and chronic respiratory disease." Arch Intern Med 1973;131:148-155.
Monostori, et al., Determination of glutathione and glutathione disulfide in biological samples: an in-depth review. J Chrom B, 877 (2009) 3331-3346.
Moore, et al., A new LC-MS/MS method for the clinical determination of reduced and oxidized glutathione from whole blood. J Chrom B, 929 (2013) 51-55.
Nakagami, et al. "A novel Nrf2 activator from microbial transformation inhibits radiation-induced dermatitis in mice," Journal of Radiation Research, vol. 57, No. 5, 2016, pp. 567-571.
Nash, et al., "Nebulized and oral thiol derivatives for pulmonary disease in cystic fibrosis." Cochrane Database Syst Rev 2009;(1):CD007168.

(56) References Cited

OTHER PUBLICATIONS

New, et al., Evaluation of BEH C18, BEH HILIC, and HSS T3 (C18) Column Chemistries for the UPLC-MS-MS Analysis of Glutathione, Glutathione Disulfide, and Ophthalmic Acid in Mouse Liver and Human Plasma. J Chrom Sci, 46 (2008) 209-214.
Nozal, et al., "Determination of glutathione, cysteine, and N-acetylcysteine in rabbit eye tissues using high-performance liquid chromatography and post-column derivatization with 5,5''-dithiobis(2-nitrobenzoic acid). J Chrom A, 778 (1997) 347-353.
University of Sao Paulo, et al. "N-Acetyl Cysteine for Cystinosis Patients", ClinicalTrials.gov [online], identifier NCT01614431, Last update posted: Jun. 20, 2012, htps://clinicaltrials.gov/ct2/show/NCT01614431, [retrieved online Jul. 9, 2021].
Tobwala, et al., "N-AcetylcysteineAmide (NACA), a Novel GSH Prodrug: Its Metabolism and Implications in Health", ISBN:978-1-62417-5, Nova Science Publishers, 2013.
Betteridge, What is Oxidative Stress? Metabolism, vol. 49, No. 2, Feb. 2000, pp. 3-8.
K. Boone, "The K-Zone: Biophysical Data Tables", 1994-2006.
Maeda et al., "Important Role of the 3-Mercaptopropionamide . . . ", JOC Article, 2005. 70. 8338-8343.
Niemeyer, "Selective Rod-and Cone-ERG Responses in Retinal Degenerations", Digital Journal of Ophthalmology, 1998, vol. 4, No. 10, 1998.
Sekhon, "Exploiting the Power of Stereochemistry in Drugs . . . ", Journal of Modern Medicinal Chemistry, 2013, 10-36.
Minozzi et al., "An Insight into the Radical Thiol/Yne Coupling: The Emergence of Arylalkyne-tagged Suggars for te Direct Photoinduced Glycosylation of Cysteine Containing Peptides", J. Org. Chem, 2011, 76, 450-459.
Wang, et al., "Hyperoxia-induced lens damage in rabbit: protective effects of N-acetylcysteine." Mol Vis. 2009;15:2945-52.
Watanabe, et al., "Skin-whitening and skin-condition-improving effects of topical oxidized glutathione: a double-blind and placebo-controlled clinical trial." Clin Cosmetic Inv Dermatol. 2014;7:267-274.
Weng, Bioanalytical liquid chromatography tandem mass spectrometry methods on underivatized silica columns with aqueous/organic mobile phases. J Chrom B, 796 (2003) 209-224.
Wu, et al., "Effects of N-acetylcysteine amide (NACA, a thiol antioxidant on radiation-induced cytotoxicity in Chenese hamster ovary cells," Life Sciences (2008), 82:1122-1130.
Yu, et al., "Intraretinal oxygen levels before and after photoreceptor loss in the RCS rat." Invest Ophthalmol Vis Sci, (2000), 41(12):3999-4006.
Poole, et al., "Mucolytic agents versus placebo for chronic bronchitis or chronic obstructive pulmonary disease." Cochrane Database Syst Rev 2015;(7):CD001287).
Reyes, et al., Neuronal glutathione content and antioxidant capacity can be normalized in situ by N-acetyl cysteine concentrations attained in human cerebrospinal fluid, Neurotherapeutics, 13 (2016) 217-225.
Rubin BK. "Aerosol Medications for Treatment of Mucus Clearance Disorders Respiratory care" 2015; 60(6): 825-832.
Salamon, et al., "Medical and Dietary Uses of N-Acetylcysteine." Antioxidants 2019, 8, 111.
Stey, et al., "The effect of oral N-acetylcysteine in chronic bronchitis: a quantitative systematic review." Eur Respir J. 2000; 16(2):253-62.
Suh, et al., Clinical assay of four thiol amino acid redox couples by LC-MS/MS: utility in thalassemia, J Chrom B, 877 (2009) 3418-3427.
Sunitha, et al., N-acetylcysteine amide: a derivative to fulfull the promises of N-acetylcysteine. Free Radic Res, 47 (2013) 357-367.
Tam, et al., "Nebulized and oral thiol derivatives for pulmonary disease in cystic fibrosis." Cochrane Database Syst Rev 2013;(7):CD007168.
Tarrant et al. "Mucoactive agents for adults with acute lung conditions: A systematic review." Heart Lung (2019) 48 (2):141-147.

Tse, et al., "High-dose N-acetylcysteinine in stable COPD: the 1-year, double-blind, randomized, placebo-controlled HIACE study." Chest, (2013). 144(1):106-118.
Ates, et al., "Antioxidant and free radical scavenging properties of N-acetylcysteine amide (NACA) and comparison with N-acetylcysteine (NAC)." Free Radic Res. (2008), 42(4):372-7.
Bean, et al., "Comparative evaluation of antioxidant reactivity within obstructed and control rabbit urinary bladder tissue using FRAP and CUPRAC assays," Molecular and Cellular Biochemistry (2008) 323(1-2):139-142.
Bernardes, et al., "From Disulfide- to Thioether-Linked Glycoproteins" Angewandte Chemie, Supporting Information (2008), S1-S97.
Buss, et al., "Protein carbonyl measurement by a sensitive ELISA method." Free Radic Biol Med, (1997), 23(3):361-6.
Campochiaro, et al. "Is there Excess Oxidative Stress and Damage in Eyes of Patients with Retinitis Pigmentosa?" Antioxidants & Redox Signaling, (2015) 23(7):643-648.
Campochiaro, et al. "The Mechanism of Cone Cell Death in Retinitis Pigmentosa", Progress in Retinal and Eye Research (2018), 62:24-37.
Chastain, et al. "Distribution of topical ocular nepafenac and its active metabolite amfenac to the posterior segment of the eye." Exp Eye Res (2016), 145:58-67.
Davies, et al., "Measurements of protein carbonyls, ortho- and meta-tyrosine and oxidative phosphorylation complex activity in mitochondria from young and old rats." Free Radic Biol Med, (2001), 31(2):181-90.
Devries, et al. "N-acetyl-l-cysteine." J Cell Biochem Suppl (1993), 17F:270-277.
Dietz, et al., "Photochemical Reduction of 5-Bromouracil by Cysteine Derivatives and Coupling of 5-Bromouracil to Cystine Derivatives," Photochemistry and Photobiology (1989), 49(2):121-129.
Dong, et al., "Compared with N-acetylcysteine (NAC), N-Acetylcysteinne Amid (NACA) Provides Increased Protein of Cone Function in a Model of Retinitis Pigmentosa." Investigative Ophthalmology & Visual Science, (2014), 55:1-2. (Abstract).
Extended European Search Report for EP 15770142.6 dated Oct. 20, 2017.
Extended European Search Report for EP 15857309.7 dated May 23, 2018.
Extended European Search Report for EP 15858590.1 dated May 2, 2018.
Heymann, et al., "Preparation and some biological properties of the asparagine analog L-2-amino-2-carboxyethanesulfonamide" Journal of the American Chemical Society, (1959), 81:5125-5128.
International Search Report and Written Opinion PCT/US2015/059589 dated Feb. 2, 2016, 10 pg.
International Search Report and Written Opinion PCT/US2015/060172 dated Apr. 13, 2016, 12 pg.
International Search Report and Written Opinion PCT/US2018/052065 dated Jan. 10, 2019, 10 pg.
International Search Report and Written Opinion PCT/US2018/061357 dated Dec. 18, 2018, 11 pg.
International Search Report and Written Opinion PCT/US2018/059446 dated Dec. 31, 2018, 15 pg.
Jones, "Extracellular Redox State: Refining the Definition of Oxidative Stress in Aging," Rejuvenation Research (2006), 9(2):169-181.
Kahns, et al., "Prodrugs as drug delivery systems. 107. Synthesis and chemical and enzymatic hydrolysis kinetics of various mono- and diester prodrug of N-acetylcysteine." Int J Pharm (1990), 62:193-205.
Kelly, "Clinical applications of N-acetylcysteine." Altern Med Rev J Clin Ther. (1998), 3(2):114-27.
Komeima, et al., "Antioxidants reduce cone cell death in a model of retinitis pigmentosa." PNAS, (2006), 103 (30):11300-11305.
Komeina, et al., "Antioxidants slow photoreceptor cell death in mouse models of retinitis pigmentosa." J Cell Physiol. (2007), 213(3):809-15.
Komeina, et al., "Blockade of neuronal nitric oxide synthase reduces cone cell death in a model of retinitis pigmentosa." Free Radic Biol Med, (2008), 45(6):905-12.

(56) References Cited

OTHER PUBLICATIONS

Li, et al, "A Convenient Synthesis of Amino Acid Methyl Esters", Molecules (2008), 13:1111-1119.

Lu, et al., "Effects of Different Types of Oxidative Stress in RPE Cells," J Cell Phys (2006), 206(1):119-125.

Martin, et al, "Amides of N-Acylcysteines as Mucolytic Agents", Journal of Medicinal Chemistry (1967), 10:1172-1176.

Martinez-Fernandez De La Camara, et al., Altered Antioxidant-Oxidant Status in Aqueous Humor and Peripheral Blood of Patents with Retinitis Pigmentosa, PLOS One (2013), 8(9):E74223.

Park et al.: "Targeted and Reversible Blood-Retinal Barrier Disruption via Focused Ultrasound and Microbubbles" PLoS ONE (2012), 7(8):e42754.

Riley, et al., "Glutathione in the aqueous humor of human and other species." Investigative ophthalmology & visual science, (1980), 9(1):94-96.

Schimel, et al., "N-Acetylcysteine Amide (NACA) Prevents Retinal Degeneration by Up-Regulating Reduced 2 Glutathione Production and Reversing Lipid Peroxidation." The American Journal of Pathology, (2011 ), 178 D?):2032-2043.

Shen, et al., "Oxidative damage is a potential cause of cone cell death in retinitis pigmentosa." J Cell Physiol, (2005), 203(3):457-64.

Shen, et al., "Oxidative damage in age-related macular degeneration," Histology and Histopathology (2007), 22 (12):1301-1308.

Shintani, et al., "Review and Update: Current treatment trends for Patients with Retinitis Pigmentosa," Optometry (2009), 80:384-401.

Supelco "Methanolic H2S04 (10./o v/v)" 1997, Sigma-Aldrich Co., 2 Pages.

Luson, et al., "Overexpression of CERKL, a gene responsible for retinitis pigmentosa in humans, protects cells from apoptosis induced by oxidative stress." Mol Vis. (2009), 15:168-80.

Usui, et al., "Overexpression of SOD in retina: Need for increase in H202-detoxifying enzyme in same cellular compartment," Free Radical Biology and Medicine (2011 ), 51(7): 1347-1354.

Usui, et al. , "Increased expression of catalase and superoxide dismutase 2 reduces cone cell death in retinitis pigmentosa." Mol Ther JAm Soc Gene Ther. (2009), 17(5):778-86.

Usui, et al. , "NADPH oxidase plays a central role in cone cell death in retinitis pigmentosa." J Neurochem. (2009), (3):1028-37.

Canadian Patent Office, Examination Report for Appl. No. 3,046,363 dated Jun. 6, 2022, 4 pp.

\* cited by examiner

Step 3 Generation of diNACA.

METHODS OF MAKING DEUTERIUM-ENRICHED N-ACETYLCYSTEINE AMIDE (D-NACA) AND (2R, 2R')-3,3'-DISULFANEDIYL BIS(2-ACETAMIDOPROPANAMIDE) (DINACA) AND USING D-NACA AND DINACA TO TREAT DISEASES INVOLVING OXIDATIVE STRESS

CROSS-REFERENCE TO RELATED APPLICATIONS

This application claims priority to U.S. Ser. No. 16/180,984, filed Nov. 5, 2018, and claims benefit of U.S. Provisional Application Ser. No. 62/583,984, filed Nov. 9, 2017 and U.S. Provisional Application Ser. No. 62/587,246, filed Nov. 16, 2018, the entire contents of which are incorporated herein by reference.

STATEMENT OF FEDERALLY FUNDED RESEARCH

None.

TECHNICAL FIELD OF THE INVENTION

The present invention relates in general to the field of making (2R,2R')-3,3'-disulfanediyl bis(2-acetamidopropanamide) (diNACA), pharmaceutical compositions, and methods of making and using NACA-$d_3$ to treat diseases associated with oxidative damage including, but not limited to, antivenom, beta-thallassemia, cataract, chronic obstructive pulmonary disease, macular degeneration, contrast-induced nephropathy, asthma, lung contusion, methamphetamine-induced oxidative stress, multiple sclerosis, Parkinson's disease, platelet apoptosis, Tardive dyskinesia, Alzheimer disease, HIV-1-associated dementia, mitochondrial diseases, myocardial myopathy, neurodegenerative diseases, pulmonary fibrosis, retinitis pigmentosa, age-related macular degeneration, skin pigmentation, skin in need of rejuventation, antimicrobial infection, and/or Friedreich's ataxia.

BACKGROUND OF THE INVENTION

Without limiting the scope of the invention, its background is described in connection with treating oxidative stress in the eye.

One example of an eye disease is Retinitis Pigmentosa (RP), which is the term used for a genetically heterogeneous group of inherited retinal degenerations. In eye disorders caused by oxidative stress an example of an inciting event is a mutation that leads to the death of rod photoreceptors, initially causing night blindness. Rods are the major consumers of oxygen in the retina and the loss of rods causes an increase in the tissue oxygen level in the outer retina. This activates NADPH oxidase causing accumulation of superoxide radicals in the cytosol and also increases their generation in mitochondria of cones. The excess superoxide radicals overwhelm superoxide dismutase 1 and 2 (SOD1 and SOD2) and cause a chain reaction by which other free radicals are generated including some that are even more damaging than superoxide radicals, such as hydroxyl radicals and peroxynitrite. The free radicals attack proteins, lipids, and DNA causing specific modifications that indicate that oxidative damage has occurred. Oxidative damage to lipids results in lipid hydroperoxides that break down to form 4-hydroxynonenal, malondialdehyde (MDA), and acrolein. The most common modification to proteins from oxidative damage is the formation of carbonyl adducts. Measurements of these markers of oxidative damage, such as MDA or the carbonyl adducts, provide a quantitative assessment of the amount of oxidative damage that has occurred in a tissue. These modifications can impair the function of macromolecules and while there are endogenous repair processes, they are overwhelmed by severe oxidative stress resulting in reduced cellular function and eventually apoptosis. After rods are eliminated from the photoreceptor layer, oxidative stress in the outer retina is severe and leads to gradual cone cell death usually starting in the midperiphery where cone density is low and then spreading peripherally and posteriorly (centrally). The posterior spread of cone death results in constriction of the visual field and eventually a central island of vision and its elimination causes blindness.

Currently, there is no approved therapy that stops the evolution of the disease or restores vision. The therapeutic approach is restricted to slowing down the degenerative process by sunlight protection and vitamin A supplementation, treating complications (cataract and macular edema), and helping patients to cope with the social and psychological impact of blindness. Although the Argis II Retinal Prosthesis System was approved by FDA in 2013 as an implanted Humanitarian device (HUD) to treat adults with several RP, it only produces the sensation of light, thereby helping patients identify the location or movement of objects and people; the device is not disease modifying. Based on studies in animal models described below, NACA is able to treat RP in vivo.

As such, there still exists a need for novel compositions and methods for treatment of retinitis pigmentosa.

SUMMARY OF THE INVENTION

In one embodiment, the present invention includes a pharmaceutical composition comprising (2R,2R')-3,3'-disulfanediyl bis(2-acetamidopropanamide)(diNACA) and derivatives or solids thereof. In one aspect, the (2R,2R')-3,3'-disulfanediyl bis(2-acetamidopropanamide) has the following formula:

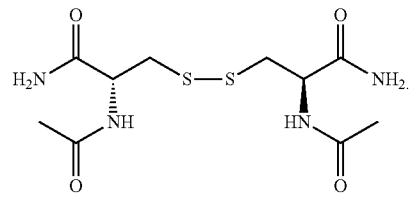

Di-NACA
$C_{10}H_{18}N_4O_4S_2$
Mol Wt: 322.40

In another aspect, the (2R,2R')-3,3'-disulfanediyl bis(2-acetamidopropanamide) and derivatives or solids thereof comprises 0.1 mole percent (mol %) to 97 mol % of (2R,2R')-3,3'-disulfanediyl bis(2-acetamidopropanamide). In another aspect, the (2R,2R')-3,3'-disulfanediyl bis(2-acetamidopropanamide) and derivatives or solids thereof comprises 5 mol % to 95 mol % of the (2R,2R')-3,3'-disulfanediyl bis(2-acetamidopropanamide). In another aspect, the (2R,2R')-3,3'-disulfanediyl bis(2-acetamidopropanamide) and derivatives or solids thereof comprises 78 mol % to 95 mol % of (2R,2R')-3,3'-disulfanediyl bis(2-acetamidopropanamide). In another aspect, the (2R,2R')-3,3'-disulfanediyl bis(2-acetamidopropanamide) and derivatives or solids thereof comprises 88 mol % to 92 mol % of (2R,2R')-3,3'-disulfanediyl bis(2-acetamidopropanamide). In another aspect, the (2R,2R')-3,3'-disulfanediyl bis(2-acetamidopropanamide) and derivatives or solids thereof comprises 78 mol % to 82 mol % of (2R,2R')-3,3'-disulfanediyl bis(2-acetamidopropanamide). In another aspect, the (2R,2R')-3,3'-disulfanediyl bis(2-acetamidopropanamide) and derivatives or solids thereof comprises 90 mol % of (2R,2R')-3,3'-disulfanediyl bis(2-acetamidopropanamide) and 10 mol % of (2R,2R')-3,3'-disulfanediyl bis(2-acetamidopropanamide). In another aspect, the (2R,2R')-3,3'-disulfanediyl bis(2-acetamidopropanamide) and derivatives or solids thereof comprises 80 mol % of (2R,2R')-3,3'-disulfanediyl bis(2-acetamidopropanamide) and 20 mol % of (2R,2R')-3,3'-disulfanediyl bis(2-acetamidopropanamide). In another aspect, the (2R,2R')-3,3'-disulfanediyl bis(2-acetamidopropanamide) and derivatives or solids thereof comprises 85 mol % of (2R,2R')-3, (2R,2R')-3,3'-disulfanediyl bis(2-acetamidopropanamide)N-acetyl cysteine amide. In another aspect, the (2R,2R')-3,3'-disulfanediyl bis(2-acetamidopropanamide) and derivatives or solids thereof comprises 70 mol % of (2R,2R')-3,3'-disulfanediyl bis(2-acetamidopropanamide) and 30 mol % of (2R,2R')-3,3'-disulfanediyl bis(2-acetamidopropanamide). In another aspect, the pharmaceutical composition further comprises a pharmaceutically acceptable adjuvant or additive. In another aspect, the diNACA is enantiopure (2R,2R')-3,3'-disulfanediyl bis(2-acetamidopropanamide). In another aspect, the diNACA is enantiopure (2S,2S')-3,3'-disulfanediyl bis(2-acetamidopropanamide). In another aspect, the diNACA is a racemic mixture of (2R,2R')-3,3'-disulfanediyl bis(2-acetamidopropanamide) and (2S,2S')-3,3'-disulfanediyl bis(2-acetamidopropanamide). In another aspect, the diNACA is enantiopure (2R,2R')-3,3'-disulfanediyl bis(2-acetamidopropanamide). In another aspect, the diNACA is enantiopure (2S,2S')-3,3'-disulfanediyl bis(2-acetamidopropanamide). In another aspect, the diNACA is a racemic mixture of (2R,2R')-3,3'-disulfanediyl bis(2-acetamidopropanamide) and (2S,2S')-3,3'-disulfanediyl bis(2-acetamidopropanamide).

In another embodiment, the present invention includes a method of treating a disease associated with oxidative damage, comprising administering a pharmaceutical composition comprising (2R,2R')-3,3'-disulfanediyl bis(2-acetamidopropanamide)(diNACA) to a patient in need thereof. In one aspect, the disease is an eye disease or disorder. In another aspect, the disease is retinitis pigmentosa. In another aspect, the disease is antivenom, beta-thallassemia, cataract, chronic obstructive pulmonary disease, macular degeneration, contrast-induced nephropathy, asthma, lung contusion, methamphetamine-induced oxidative stress, multiple sclerosis, Parkinson's disease, platelet apoptosis, Tardive dyskinesia, Alzheimer disease, HIV-1-associated dementia, mitochondrial diseases, myocardial myopathy, neurodegenerative diseases, pulmonary fibrosis, Friedreich's ataxia.

In another embodiment, the present invention includes a method of making (2R,2R')-3,3'-disulfanediyl bis(2-acetamidopropanamide) (DiNACA) comprising the steps of: forming L-Cystine Dimethylester Dihydrochloride from L-cystine by the following reaction:

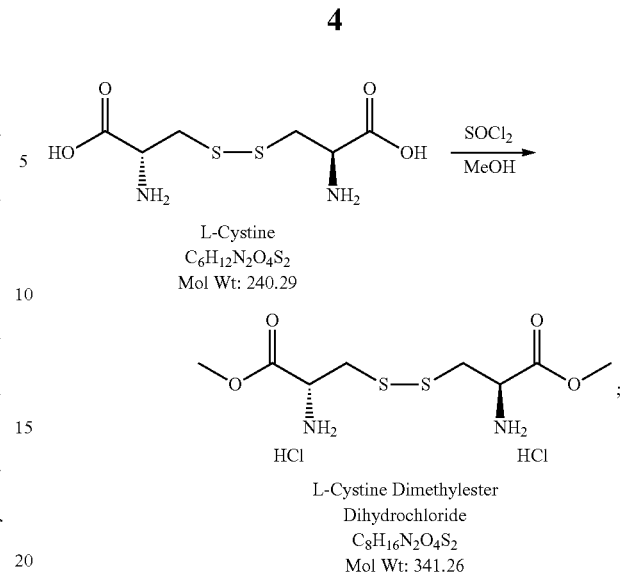

forming Di-NACMe from L-Cystine Dimethylester Dihydrochloride by the following reaction:

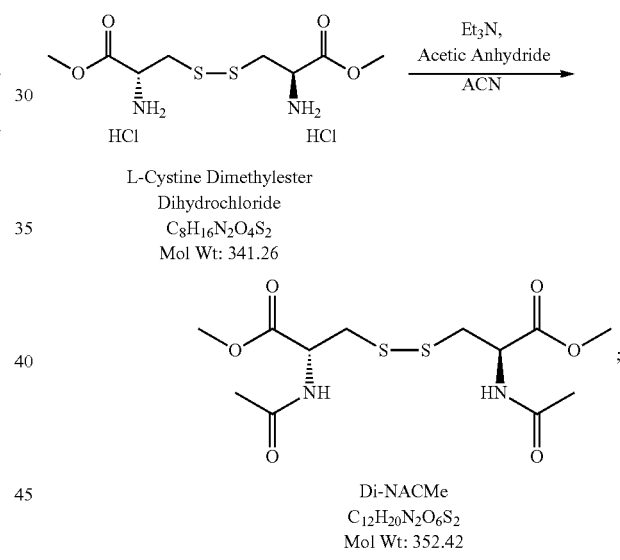

generating DiNACA from Di-NACMe by the following reaction:

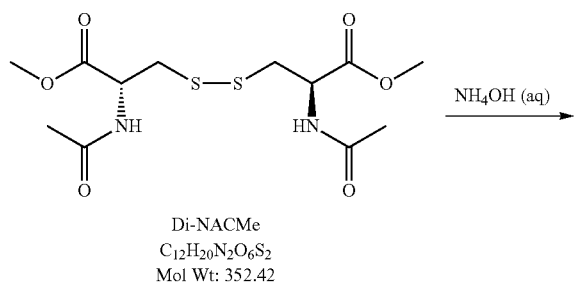

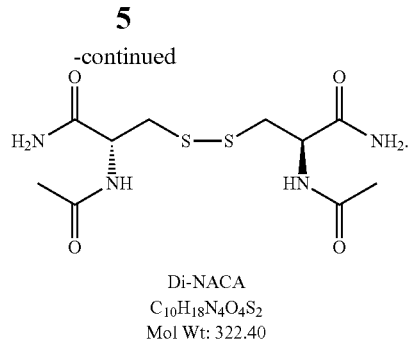

Di-NACA
C$_{10}$H$_{18}$N$_4$O$_4$S$_2$
Mol Wt: 322.40

In one aspect, the methods further comprises the step of purifying the DiNACA by the following reaction:

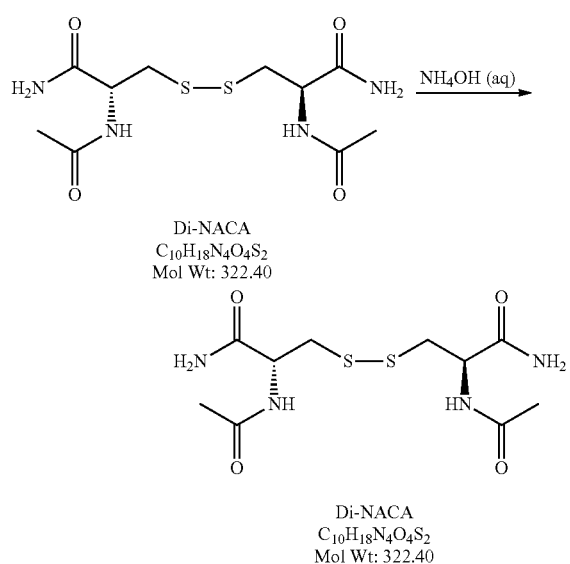

Di-NACA
C$_{10}$H$_{18}$N$_4$O$_4$S$_2$
Mol Wt: 322.40

Di-NACA
C$_{10}$H$_{18}$N$_4$O$_4$S$_2$
Mol Wt: 322.40

In another aspect, the purified diNACA comprises 0.1 mol % to 97 mol % of (2R,2R')-3,3'-disulfanediyl bis(2-acetamidopropanamide). In another aspect, the purified diNACA comprises 5 mol % to 95 mol % of the (2R,2R')-3,3'-disulfanediyl bis(2-acetamidopropanamide). In another aspect, the purified diNACA comprises 78 mol % to 95 mol % of (2R,2R')-3,3'-disulfanediyl bis(2-acetamidopropanamide). In another aspect, the purified diNACA comprises 88 mol % to 92 mol % of (2R,2R')-3,3'-disulfanediyl bis(2-acetamidopropanamide). In another aspect, the purified DiNACA comprises 78 mol % to 82 mol % of (2R,2R')-3, 3'-disulfanediyl bis(2-acetamidopropanamide). In another aspect, the purified diNACA comprises 90 mol % of (2R, 2R')-3,3'-disulfanediyl bis(2-acetamidopropanamide) and 10 mol % of (2R,2R')-3,3'-disulfanediyl bis(2-acetamidopropanamide). In another aspect, the purified diNACA comprises 80 mol % of (2R,2R')-3,3'-disulfanediyl bis(2-acetamidopropanamide) and 20 mol % of (2R,2R')-3,3'-disulfanediyl bis(2-acetamidopropanamide). In another aspect, the purified diNACA comprises 85 mol % of (2R, 2R')-3, (2R,2R')-3,3'-disulfanediyl bis(2-acetamidopropanamide)N-acetyl cysteine amide. In another aspect, the purified DiNACA comprises 70 mol % of (2R,2R')-3,3'-disulfanediyl bis(2-acetamidopropanamide) and 30 mol % of (2R,2R')-3,3'-disulfanediyl bis(2-acetamidopropanamide). In another aspect, the method further comprises the step of formulating a pharmaceutical composition by mixing the diNACA with a pharmaceutically acceptable adjuvant or additive.

In one embodiment, the present invention includes a pharmaceutical composition comprising deuterated N-acetylcysteine amide (NACA-d$_3$), or a physiologically acceptable salt thereof, having a deuterium enrichment above the natural abundance of deuterium; and D$_3$-N-acetyl cysteine amide, or a physiologically acceptable derivative thereof, having a deuterium enrichment above the natural abundance of deuterium. In one aspect, the deuterated N-acetylcysteine amide has the following formula:

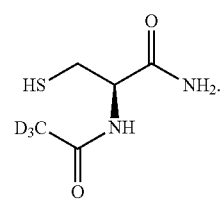

In another aspect, the pharmaceutical composition may comprise 0.1 mole/percent (mol %) to 97 mol % of the D$_3$-N-acetyl cysteine amide. In another aspect, the pharmaceutical composition may comprise 5 mol % to 95 mol % of the D$_3$-N-acetyl cysteine amide. In another aspect, the pharmaceutical composition may comprise 78 mol % to 95 mol % of the D$_3$-N-acetyl cysteine amide. In another aspect, the pharmaceutical composition may comprise 88 mol % to 92 mol % of the D$_3$-N-acetyl cysteine amide. In another aspect, the pharmaceutical composition may comprise 78 mol % to 82 mol % of the D$_3$-N-acetyl cysteine amide. In another aspect, the pharmaceutical composition may comprise 90 mol % of the D$_3$-N-acetyl cysteine and 10 mol % of the N-acetyl cysteine amide. In another aspect, the pharmaceutical composition may comprise 80 mol % of the D$_3$-N-acetyl cysteine and 20 mol % of the N-acetyl cysteine amide. In another aspect, the pharmaceutical composition may comprise 85 mol % of the D$_3$-N-acetyl cysteine amide and 15 mol % of the N-acetyl cysteine amide. In another aspect, the pharmaceutical composition may comprise 70 mol % of the D$_3$-N-acetyl cysteine amide and 30 mol % of the N-acetyl cysteine amide. In another aspect, the deuterium enrichment in D3-position in the D$_3$-N-acetyl cysteine amide is about 90 mol % to 98 mol %. In another aspect, the difference in the deuterium enrichment in the D3-positions in the D$_3$-N-acetyl cysteine is about 8 to 10 percentage points. In another aspect, the pharmaceutical composition may further comprise a pharmaceutically acceptable adjuvant or additive. In another aspect, the pharmaceutical composition may comprise deuterium enrichment above the natural abundance of deuterium is within a predefined range of 0.02 mol % to 100 mol % deuterium, as determined by NMR spectroscopy in d$_6$-dimethyl sulfoxide using a 500 MHz spectrometer. In another aspect, the NACA-d$_3$ is enantiopure (R)-2-acetylamino-3-mercapto-propamide. In another aspect, the NACA-d$_3$ is enantiopure (S)-2-acetylamino-3-mercapto-propamide. In another aspect, the NACA-d$_3$ is a racemic mixture of (R)-2-acetylamino-3-mercapto-propamide and (S)-2-acetylamino-3-mercapto-propamide.

In another embodiment, the present invention includes a method of treating a disease associated with oxidative damage, comprising administering a pharmaceutical composition of claim 1 to a patient in need thereof. In one aspect, the disease is a disease of the eye. In another aspect, the disease is retinitis pigmentosa. In another aspect, the disease is antivenom, beta-thallassemia, cataract, chronic obstructive pulmonary disease, macular degeneration, contrast-induced nephropathy, asthma, lung contusion, methamphetamine-induced oxidative stress, multiple sclerosis, Parkinson's disease, platelet apoptosis, Tardive dyskinesia, Alzheimer disease, HIV-1-associated dementia, mitochondrial diseases, myocardial myopathy, neurodegenerative diseases, pulmonary fibrosis, or Friedreich's ataxia.

In another embodiment, the present invention includes a method of making deuterium enriched N-acetylcysteine amide (NACA-$d_3$) comprising the steps of:

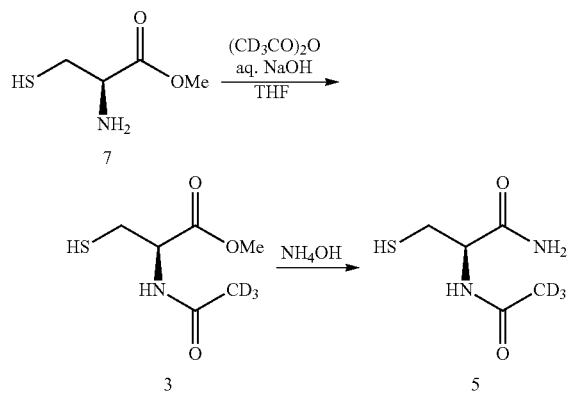

In another embodiment, the present invention includes a method of making deuterium enriched N-acetylcysteine amide (NACA-$d_3$) comprising the steps of:

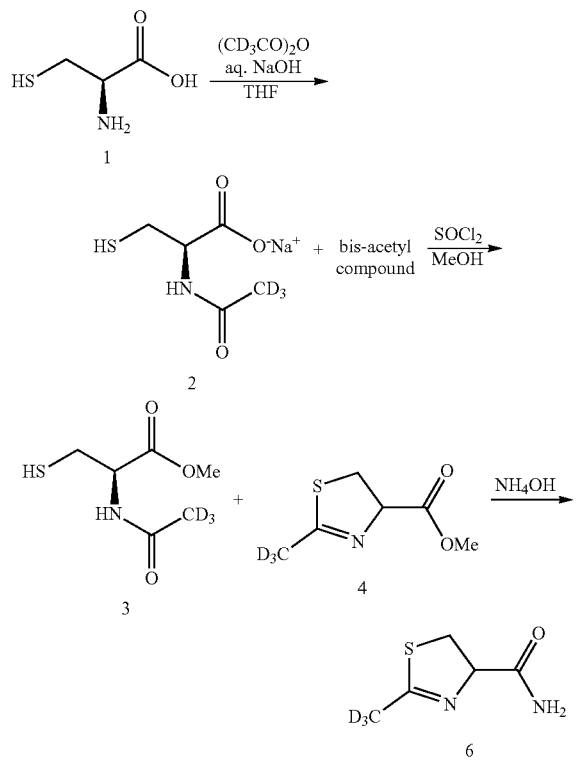

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

Figure 1:
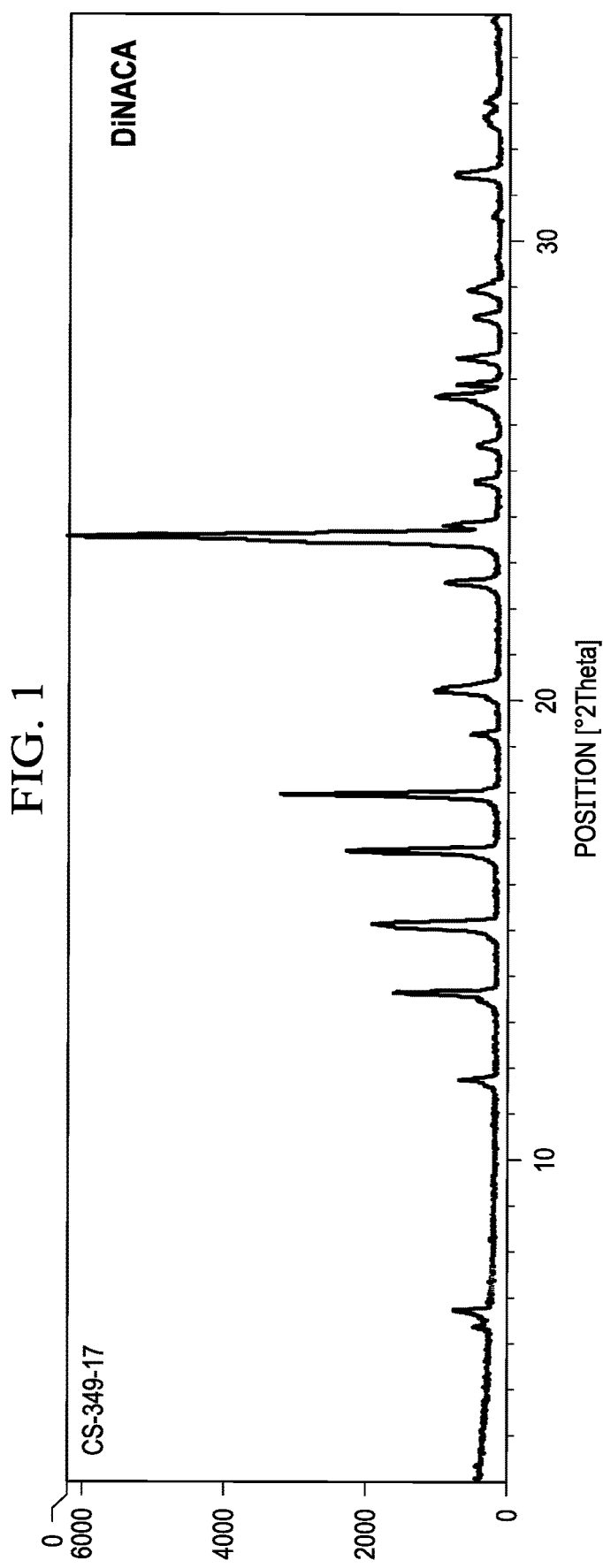
FIG. 1 is an X-Ray Powder Diffractogram for (2R,2R')-3,3'-disulfanediyl bis(2-acetamidopropanamide) of the present invention.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not limit the invention, except as outlined in the claims.

This invention pertains to (2R,2R')-3,3'-disulfanediyl bis (2-acetamidopropanamide), which is also known as diNACA, diNaca, di-NACA, DiNACA, Di-NACA, dimer of NACA, NACA dimer, NACA disulfide, each of which is used interchangeably herein.

This invention pertains to deuterated N-acetylcysteine amide, also known as deuterated NPI-001, deuterated NACA, deuterated AD4, deuterated BB-001, deuterated (R)-2-acetylamino)-3-mercapto-propamide, deuterated N-acetyl-L-cysteinamide, or deuterated acetylcysteineamide. This invention pertains to deuterated N-acetylcysteine amide, deuterated NPI-001, deuterated NACA, deuterated AD4, deuterated BB-001, deuterated (R)-2-acetylamino-3-mercapto-propamide, deuterated N-acetyl-L-cysteinamide, or deuterated acetylcysteineamide, all of which are used interchangeably.

This invention also pertains to NACA-$d_3$ treatment of eye diseases associated with oxidative damage, but also other diseases associated with oxidative damage including, but not limited to, antivenom, beta-thallassemia, cataract, chronic obstructive pulmonary disease, macular degeneration, contrast-induced nephropathy, asthma, lung contusion, methamphetamine-induced oxidative stress, multiple sclerosis, Parkinson's disease, platelet apoptosis, Tardive dyskinesia, Alzheimer disease, HIV-1-associated dementia, mitochondrial diseases, myocardial myopathy, neurodegenerative diseases, pulmonary fibrosis, Friedreich's ataxia.

As used herein, the term "deuterium-enriched" refers to the feature that the compound has a quantity of deuterium that is greater than in naturally occurring compounds or synthetic compounds prepared from substrates having the naturally occurring distribution of isotopes. The invention provides deuterium-enriched, deuterated-N-acetyl cysteine amide, pharmaceutical compositions, and methods of treating eye disorders, and other medical disorders using, e.g., an enantiopure or enantio-enriched deuterium-enriched $D_3$-N-acetyl cysteine amide (NACA-$d_3$). The threshold amount of deuterium enrichment is specified in certain instances in this disclosure, and all percentages given for the amount of deuterium present are mole percentages.

As used herein, the term "effective amount" refers to the amount of a compound sufficient to effect beneficial or desired results. An effective amount can be administered in one or more administrations, applications or dosages and is not intended to be limited to a particular formulation or administration route. As used herein, the term "treating" includes any effect, e.g., lessening, reducing, modulating, ameliorating or eliminating, that results in the improvement of the eye condition, eye disease, eye disorder, and the like, or ameliorating a symptom thereof.

As used herein, the term "therapeutically effective amount" refers to an amount of a compound of the invention that is effective when administered alone or in combination to treat the desired condition or disorder. A "therapeutically effective amount" includes an amount of the combination of compounds claimed that is effective to treat the desired condition or disorder. The combination of compounds can be additive and is preferably a synergistic combination. Synergy occurs when the effect of the compounds when administered in combination is greater than the additive effect of the compounds when administered alone as a single agent. In general, a synergistic effect is most clearly demonstrated at sub-optimal concentrations of the compounds. Synergy can be in terms of lower incidence of adverse side effects and/or toxicity, increased efficacy, or some other beneficial effect of the combination compared with the individual components.

DiNACA is typically administered in admixture with suitable pharmaceutical salts, buffers, diluents, extenders, excipients and/or carriers (collectively referred to herein as a pharmaceutically acceptable carrier or carrier materials) selected based on the intended form of administration and as consistent with conventional pharmaceutical practices. Depending on the best location for administration, diNACA may be formulated to provide, e.g., maximum and/or consistent dosing for the particular form for oral, rectal, topical (including ophthalmic), inhalation, intranasal, injection (intravenous or intraocular) or parenteral administration. While diNACA may be administered alone, it will generally be provided in a stable form mixed with a pharmaceutically acceptable carrier. The carrier may be solid or liquid, depending on the type and/or location of administration selected.

Techniques and compositions for making useful dosage forms using the present invention are described in one or more of the following references: Anderson, Philip O.; Knoben, James E.; Troutman, William G, eds., Handbook of Clinical Drug Data, Tenth Edition, McGraw-Hill, 2002; Pratt and Taylor, eds., Principles of Drug Action, Third Edition, Churchill Livingston, N.Y., 1990; Katzung, ed., Basic and Clinical Pharmacology, Ninth Edition, McGraw Hill, 2007; Goodman and Gilman, eds., The Pharmacological Basis of Therapeutics, Tenth Edition, McGraw Hill, 2001; Remington's Pharmaceutical Sciences, 20th Ed., Lippincott Williams & Wilkins., 2000; Martindale, The Extra Pharmacopoeia, Thirty-Second Edition (The Pharmaceutical Press, London, 1999); all of which are incorporated by reference, and the like, relevant portions incorporated herein by reference.

For example, DiNACA may be included in a tablet. Tablets may contain, e.g., suitable binders, lubricants, disintegrating agents, coloring agents, flavoring agents, flow-inducing agents and/or melting agents. For example, oral administration may be in a dosage unit form of a tablet, gelcap, caplet or capsule, the active drug component being combined with an non-toxic, pharmaceutically acceptable, inert carrier such as lactose, gelatin, agar, starch, sucrose, glucose, methyl cellulose, magnesium stearate, dicalcium phosphate, calcium sulfate, mannitol, sorbitol, mixtures thereof, and the like. Suitable binders for use with the present invention include: starch, gelatin, natural sugars (e.g., glucose or beta-lactose), corn sweeteners, natural and synthetic gums (e.g., acacia, tragacanth or sodium alginate), carboxymethylcellulose, polyethylene glycol, waxes, and the like. Lubricants for use with the invention may include: sodium oleate, sodium stearate, magnesium stearate, sodium benzoate, sodium acetate, sodium chloride, mixtures thereof, and the like. Disintegrators may include: starch, methyl cellulose, agar, bentonite, xanthan gum, mixtures thereof, and the like.

DiNACA may be administered in the form of liposome delivery systems, e.g., small unilamellar vesicles, large unilamallar vesicles, and multilamellar vesicles, whether charged or uncharged. Liposomes may include one or more: phospholipids (e.g., cholesterol), stearylamine and/or phosphatidylcholines, mixtures thereof, and the like.

DiNACA may also be coupled to one or more soluble, biodegradable, bioacceptable polymers as drug carriers or as a prodrug. Such polymers may include: polyvinylpyrrolidone, pyran copolymer, polyhydroxylpropylmethacrylamide-phenol, polyhydroxyethylasparta-midephenol, or poly-ethyleneoxide-polylysine substituted with palmitoyl residues, mixtures thereof, and the like. Furthermore, diNACA may be coupled one or more biodegradable polymers to achieve controlled release of the diNACA, biodegradable polymers for use with the present invention include: polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels, mixtures thereof, and the like.

As used herein, the term "pharmaceutically acceptable salts" refers to derivatives of the disclosed compounds, wherein the parent compound is modified by making acid or base salts thereof. Examples of pharmaceutically acceptable salts include, but are not limited to, mineral or organic acid salts of the basic residues. The pharmaceutically acceptable salts include the conventional quaternary ammonium salts of the parent compound formed, for example, from non-toxic inorganic or organic acids. These salts can be prepared in situ in the administration vehicle or the dosage form manufacturing process, or by separately reacting a purified compound of the invention in its free base form with a suitable organic or inorganic acid, and isolating the salt thus formed during subsequent purification. For example, such conventional non-toxic salts include, but are not limited to, those derived from inorganic and organic acids selected from 1,2-ethanedisulfonic, 2-acetoxybenzoic, 2-hydroxyethanesulfonic, acetic, ascorbic, benzenesulfonic, benzoic, bicarbonic, bisulfonic, carbonic, citric, edetic, ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauric, lauryl sulfonic, maleic, malic, mandelic, methanesulfonic, napsylic, naphthylic, nitric, oleic, oxalic, palimitic, pamoic, pantothenic, phenylacetic, phosphoric, polygalacturonic, propionic, salicyclic, stearic, succinic, sulfamic, sulfanilic, sulfuric, tannic, tartaric, toluenesulfonic, and valeric.

A dosage unit for use of the deuterated-N-acetyl cysteine amide of the present invention, may be a single compound or mixtures thereof with other compounds, e.g., a potentiator. The compounds may be mixed together, form ionic or even covalent bonds. The deuterated-N-acetyl cysteine amide of the present invention may be administered in oral, intravenous (bolus or infusion), intraperitoneal, subcutaneous, or intramuscular form, all using dosage forms well known to those of ordinary skill in the pharmaceutical arts. Depending on the particular location or method of delivery, different dosage forms, e.g., tablets, capsules, pills, powders, granules, elixirs, tinctures, suspensions, syrups, gels, solutions, and emulsions may be used to provide the deuterated-N-acetyl cysteine amide of the present invention to a patient in need of therapy that includes $D_3$-N-acetyl cysteine amide.

Deuterated-N-acetyl cysteine amide is typically administered in admixture with suitable pharmaceutical salts, buffers, diluents, extenders, excipients and/or carriers (collectively referred to herein as a pharmaceutically acceptable carrier or carrier materials) selected based on the intended form of administration and as consistent with conventional pharmaceutical practices. Depending on the best location for administration, the deuterated-N-acetyl cysteine amide may be formulated to provide, e.g., maximum and/or consistent dosing for the particular form for oral, rectal, topical (including ophthalmic), inhalation, intranasal, injection (intravenous or intraocular) or parenteral administration. While the deuterated-N-acetyl cysteine amide may be administered alone, it will generally be provided in a stable form or derivatives thereof mixed with a pharmaceutically acceptable carrier. The carrier may be solid or liquid, depending on the type and/or location of administration selected.

The skilled artisan will recognize that deuterium ($^2$H) is a stable, non-radioactive isotope of $^1$H hydrogen and has an atomic weight of 2.014. Hydrogen naturally occurs as a mixture of the isotopes: hydrogen ($^1$H), deuterium ($^2$H), and tritium ($^3$H). The skilled artisan recognizes that in all chemical compounds with an H atom, the H atom actually represents a mixture of $^1$H, $^2$H, and $^3$H, where about 0.015% is deuterium. Thus, compounds with a level of deuterium that has been enriched to be greater than its natural abundance of 0.015% are considered unnatural and, as a result, novel over their non-enriched counterparts.

The deuterium-enriched $D_3$-N-acetyl cysteine amide described herein includes deuterium enrichment for $D_3$-N-acetyl cysteine amide and optionally in other locations in the compound. Deuterium-enrichment reduces the rate at which the two enantiomers of $D_3$-N-acetyl cysteine amide may interconvert. Further, the deuterium-enriched $D_3$-N-acetyl cysteine amide described herein is provided in enantiomerically pure form. This enantiomerically pure, deuterium-enriched $D_3$-N-acetyl cysteine amide provides for a better therapeutic agent than non-deuterated $D_3$-N-acetyl cysteine amide and/or racemic mixtures of the compound.

The present invention provides deuterium-enriched compounds for use in the therapeutic methods and pharmaceutical compositions described herein. The deuterium-enriched compounds are provided in high enantiomeric purity in order to maximize therapeutic benefit, such as maximal potency per dose of therapeutic agent and minimize adverse side effects, such as off-target effects.

In one embodiment, gelatin capsules (gelcaps) may include deuterated-N-acetyl cysteine amide, diNACA, or both and powdered carriers, such as lactose, starch, cellulose derivatives, magnesium stearate, stearic acid, and the like. Like diluents may be used to make compressed tablets. Both tablets and capsules may be manufactured as immediate-release, mixed-release or sustained-release formulations to provide for a range of release of medication over a period of minutes to hours. Compressed tablets may be sugar coated or film coated to mask any unpleasant taste and protect the tablet from the atmosphere. An enteric coating may be used to provide selective disintegration in, e.g., the gastrointestinal tract.

The deuterated-N-acetyl cysteine amide, diNACA, or both may be administered in the form of liposome delivery systems, e.g., small unilamellar vesicles, large unilamallar vesicles, and multilamellar vesicles, whether charged or uncharged. Liposomes may include one or more: phospholipids (e.g., cholesterol), stearylamine and/or phosphatidylcholines, mixtures thereof, and the like.

The deuterated-N-acetyl cysteine amide, diNACA, or both may also be coupled to one or more soluble, biodegradable, bioacceptable polymers as drug carriers or as a prodrug. Such polymers may include: polyvinylpyrrolidone, pyran copolymer, polyhydroxylpropylmethacrylamide-phenol, polyhydroxyethylasparta-midephenol, or polyethylene-oxide-polylysine substituted with palmitoyl residues, mixtures thereof, and the like. Furthermore, the deuterated-N-acetyl cysteine amide may be coupled one or more biodegradable polymers to achieve controlled release of the deuterated-N-acetyl cysteine amide, biodegradable polymers for use with the present invention include: polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels, mixtures thereof, and the like.

Oral Solutions or Suspensions. For oral administration in a liquid dosage form, the oral drug components may be combined with any oral, non-toxic, pharmaceutically acceptable inert carrier such as ethanol, glycerol, water, and the like. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, surfactants, coloring agents, and melting agents, mixtures thereof, and the like.

Liquid dosage forms for oral administration may also include coloring and flavoring agents that increase patient acceptance and therefore compliance with a dosing regimen.

Parenteral Solutions. Solutions for parenteral administration include generally, a water-soluble salt of the active ingredient, suitable stabilizing agents, and if necessary, buffering salts. In general, water, a suitable oil, saline, aqueous dextrose (e.g., glucose, lactose and related sugar solutions) and glycols (e.g., propylene glycol or polyethylene glycols) may be used as suitable carriers for parenteral solutions. Antioxidizing agents such as sodium bisulfite, sodium sulfite and/or ascorbic acid, either alone or in combination, are suitable stabilizing agents. Citric acid and its salts and sodium EDTA may also be included to increase stability. In addition, parenteral solutions may include pharmaceutically acceptable preservatives, e.g., benzalkonium chloride, methyl- or propyl-paraben, and/or chlorobutanol. Suitable pharmaceutical carriers are described in Remington's Pharmaceutical Sciences, Mack Publishing Company, a standard reference text in this field, relevant portions incorporated herein by reference.

Topical Lotions, Gels, Creams, Solutions or Suspensions. For topical administration in a liquid dosage form, the drug components may be combined with numerous non-toxic, pharmaceutically acceptable inert excipients such as ethanol, glycerol, water, and some non-aqueous moieties. Formulations may be sterile or non-sterile. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, thickeners, viscosity-modifiers, surfactants, coloring agents, and melting agents, mixtures thereof, and the like.

Capsules. Capsules may be prepared by filling standard two-piece hard gelatin or hydroxypropyl methylcellulose capsules each with 10 to 500 milligrams of powdered active ingredient, 5 to 150 milligrams of lactose, 5 to 50 milligrams of cellulose and 6 milligrams magnesium stearate.

Soft Gelatin Capsules. A mixture of active ingredient is dissolved in a digestible oil such as soybean oil, cottonseed oil or olive oil. The active ingredient is prepared and injected by using a positive displacement pump into gelatin to form soft gelatin capsules containing, e.g., 100-500 milligrams of the active ingredient. The capsules are washed and dried.

Tablets. A large number of tablets are prepared by conventional procedures so that the dosage unit was 100-500 milligrams of active ingredient, 0.2 milligrams of colloidal silicon dioxide, 5 milligrams of magnesium stearate, 50-275 milligrams of microcrystalline cellulose, 11 milligrams of starch and 98.8 milligrams of lactose. Appropriate coatings may be applied to increase palatability or delay absorption.

To provide an effervescent tablet appropriate amounts of, e.g., monosodium citrate and sodium bicarbonate, are blended together and then roller compacted, in the absence of water, to form flakes that are then crushed to give granulates. The granulates are then combined with the active ingredient, drug and/or salt thereof, conventional beading or filling agents and, optionally, sweeteners, flavors and lubricants.

Injectable solution. A parenteral composition suitable for administration by injection is prepared by stirring 1.5% by weight of active ingredient in deionized water and mixed with, e.g., up to 10% by volume propylene glycol and water. The solution is made isotonic with sodium chloride and sterilized using, e.g., ultrafiltration.

Suspension. An aqueous suspension is prepared for oral administration so that each 5 ml contain 100 mg of finely divided active ingredient, 200 mg of sodium carboxymethyl cellulose, 5 mg of sodium benzoate, 1.0 g of sorbitol solution, U.S.P., and 0.025 ml of vanillin.

Inhalation or Intranasal formulation. An inhalation or intranasal formulation includes a solution, suspension, semi-solid formulation, dry powder, or other formulation administered intranasally.

Injectable Formulation. A sterile injectable formulation includes a solution or suspension that is suitable for intramuscular, intravenous, intraocular (including intravitreal or intracameral) or subcutaneous administration. Such injectable formulations are isosmotic, usually with osmaolarity similar to isotonic 0.9% saline solution, and pH balanced, usually with a neutral pH.

For mini-tablets, the active ingredient is compressed into a hardness in the range 6 to 12 Kp. The hardness of the final tablets is influenced by the linear roller compaction strength used in preparing the granulates, which are influenced by the particle size of, e.g., the monosodium hydrogen carbonate and sodium hydrogen carbonate. For smaller particle sizes, a linear roller compaction strength of about 15 to 20 KN/cm may be used.

As used herein, the term "chewable" refers to semi-soft, palatable and stable chewable treat without addition of water. It should be appreciated to the skilled artisan that a chewable composition will be stable and palatable, fast disintegrating, semi-soft medicated chewable tablets (treats) by extrusion without the addition of extraneous water. A soft chewable tablets does not harden on storage and are resistant to microbial contamination. A semi-soft chewable contain a blend of any one or more of binders, flavors, palatability enhancers, humectants, disintegrating agents, non-aqueous solvents, and diluents that are plasticized with liquid plasticizers, such as glycols and polyols to make them ductile and extrudable. The chewable can be made by extrusion, e.g., including fats or lipids as plasticizers and binding agents, is manufactured in the absence of added water, uses plasticizers to replace water in extrudable matrices, contains humectants to maintain the extrudable chew in a pliant and soft state during its shelf life, or any combination thereof. The chewable form may be provided in conjunction with one or more flavorings and/or taste masking agents that improve the taste of the formulation greater than 10, 20, 30, 40, 50, 60, 70, 80, or 90%. The chewable can include the active agent and the ion exchange resin to enhance taste masking.

Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents. Oral dosage forms optionally contain flavorings and coloring agents. Parenteral and intravenous forms may also include minerals and other materials to make them compatible with the type of injection or delivery system chosen.

Enantiopurity. The present invention covers both the R and S enantiomers of diNACA. The natural enantiomer, i.e., the enantiomer found in nature for cysteine is L-cysteine. When L-cysteine is converted by chemical synthesis to diNACA with no racemization, the result is di-L-NACA which is equivalent to (2R,2R')-3,3'-disulfanediyl bis(2-acetamidopropanamide). The opposite enantiomer is obtained when D-cysteine is converted by chemical synthesis to NACA with no racemization to yield di-D-NACA which is equivalent to (2S,2S')-3,3'-disulfanediyl bis(2-acetamidopropanamide).

Enantiopurity. The present invention covers both the R and S enantiomers of NACA-$d_3$. The natural enantiomer, i.e., the enantiomer found in nature for cysteine is L-cysteine. When L-cysteine is converted by chemical synthesis to NACA with no racemization, the result is N-acetyl-L-cysteine amide, which is equivalent to (R)-2-acetylamino-3-mercapto-propamide. The opposite enantiomer is obtained when D-cysteine is converted by chemical synthesis to NACA with no racemization to yield N-acetyl-L-cysteine amide, which is equivalent to (S)-2-acetylamino-3-mercapto-propamide.

Metabolism. An advantage of diNACA over N-acetylsysteine amide (NACA) is the reduction in metabolism rate compared to NACA. DiNACA has a longer plasma half-life than NACA. The major metabolites of diNACA are NACA and N-acetylcysteine (NAC) afforded by cleavage of the sulfur bond of diNACA to yield NACA and NAC. Dosing the patient with diNACA affords high greater bioavailability in tissues like the retina and aqueous humore compared to dosing with NACA, presumably due the higher lipophilicity of diNACA compared to NACA and the resulting in vivo cleavage to two NACA-like molecules, thereby effectively increasing the half-life of NACA in the body.

Metabolism. Deuterium-inhibition of NACA metabolism. An advantage of NACA-$d_3$ is the reduction in metabolism rate compared to the non-deuterated NACA. Non-deuterated NACA has a plasma half-life of approximately 2 hours in fasting subjects and approximately 6 hours in fed subjects. The major metabolite of NACA is N-acetylcysteine (NAC) afforded by deamidation of the primary amide functional group of NACA by tissue (e.g., plasma or other tissue) amidase. Another metabolite of NACA is cysteine afforded by (a) deamidation of the primary amide functional group of NACA by tissue (e.g., plasma or other tissue) amidase and (b) de-acetylation of the secondary amide functional group of NACA by tissue (e.g., plasma or other tissue) amidase. Replacement of the acetyl methyl group hydrogen atoms with deuterium atoms slows down the action of tissue amidases on both (primary and secondary) amide functional groups of NACA-$d_3$, thereby prolonging its residence time in the body, i.e., increasing the half-life in the body.

Example 1

Preparation of (2R,2R')-3,3'-disulfanediyl bis(2-acetamidopropanamide) (diNACA). A process for preparing (2R, 2R')-3,3'-disulfanediyl bis(2-acetamidopropanamide) is described. The inventors used various approaches to make diNACA and found the most advantageous route as shown in Steps 1-3. To generate the diNACA, Step 1 (01NPI01-01) was performed in a 2000 L glass-lined reactor using 67 kg of L-cystine. The material was treated with methanol (1323 kg, 25 vol) and thionyl chloride (80 kg, 2.41 eq) and agitated for 1 hour before heating to reflux. Once the In-Process Control (IPC) sample met the criteria of less than 1% of L-cystine remaining, the reaction was deemed complete. After cooling to 20±5° C. the methanol was exchanged with methyl t-butylether and the product isolated by filtration. Due to the scale, the isolation occurred in three portions with the first and some of the second portion being carried forward without drying. The remainder of the material was dried under vacuum to yield L-cystine dimethylester dihydrochloride.

Figure 11:
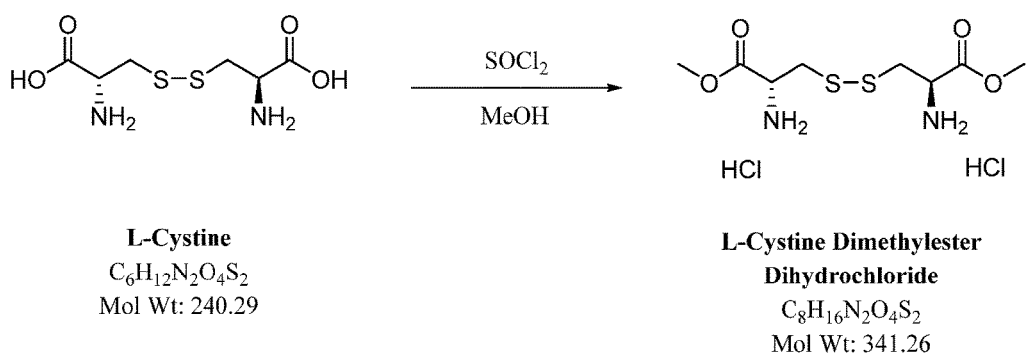
FIG. 11 shows step 1 in the formation of L-cystine dimethylester dihydrochloride.

FIG. 11 shows step 1 in the formation of L-cystine dimethylester dihydrochloride.

TABLE 1

| Reagents/Materials | MW | Eqs. | Moles | Density | Expected Amt (kg) |
|---|---|---|---|---|---|
| L-Cystine, ≥98.5% | 240.29 | 1.0 | 279 | — | 67 |
| Thinonyl Chloride, ≥97% | 118.97 | 2.41 | 672 | 1.64 | 80 |
| Methanol (MeOH), ≥99% | 32.04 | 25 vol | — | 0.79 | 1323 |
| 50%(w/w) Sodium Hydroxide, aqueous solution (for scrubber) | 40.00 | — | — | 1.515 | 25 |
| Process Water, Filtered (for scrubber) | 18.02 | — | — | 1.00 | 95 |
| Methyl-tert Butyl Ether (MTBE), ≥99% | 88.15 | 26 vol | — | 0.74 | 1287 |

TABLE 2

| Reference | 01NPI01-01 |
|---|---|

|  |  |
|---:|---|
|  | To clean 2000 L reactor charged |
| 67 kg | of L-Cystine and |
| 1323 kg | of polish filtered Methanol, began agitation. Cooled the reactor contents to −10 ± 5° C., via diaphragm pump, slowly charged |
| 80 kg | of Thinyl Chloride maintaining the internal temperature at ≤−5° C. Heated reactor contents to 20 ± 5° C. and allowed to agitate for 1 hour. Furthermore, heated reactor contents to reflux (~65 to 70° C.) and allowed to agitate for 16 hours. Reaction deemed complete by HPLC analysis. Withdrew representative sample; submitted to QC laboratory for HPLC analysis. |

TABLE 2-continued

| Reference | 01NPI01-01 | | | |
|---|---|---|---|---|
| Step 1.30 - IPC for Reaction Completion (L-Cystine ▶ L-Cystine Dimethylester Dihydrochloride) | | | | |
| 01NPI01 | L-Cystine | L-Cystine Dimethylester | Reaction | |
| −01-30 | 2.7% | 97% | Complete | |

Cooled reactor contents to 20 ± 5° C. Meanwhile, set up the reactor with a scrubber. To the scrubber charged
114 kg of 4M Sodium Sodium Hydroxide, aqueous solution. Set reactor jacket temperature to 15° C. Vacuum distilled reactor contents until 402 L remained. Through polish filter charged
3 × 297 kg of Methyl tert-Butyl Ether, continued to vacuum distill until 402 L remained in the reactor while not exceeding jacket temperature of 45° C. Set jacket temperature to 15° C., through polish filter, charged
297 kg of Methyl tert-Butyl Ether and allowed the contents to agitate with an internal temperature of 20 ± 5° C. for 1 hour. The reactor contents were filtered portionwise through Nutsche Filter and rinsed with
148.5 kg of polish filtered Methyl tert-Butyl Ether. Wet L-Cystine Dimethylester Dihydrochloride was transferred into drying trays and dried to constant weight at ≤45° C. to afford 3 portions totaling 40.6 kg of L-Cystine Dimethylester Dihydrochloride.
L-Cystine Dimethylester Dihydrochloride ready for use in the next step Step 2 was carried out in a 2000 L glass-lined reactor by treating 44 kg of L-cystine dimethylester dihydrochloride with acetonitrile (799 kg, 23 vol), cooling to 0±5° C. and sparging with nitrogen for 30 minutes. Triethylamine (55 kg, 4.2 eq) was added followed by slow addition of acetic anhydride (28 kg, 2.1 eq) while maintaining the internal temperature at <5° C. The reaction was stirred for 30 minutes and then sampled until the IPC met the criteria for completion, less than 1% of L-cystine dimethylester dihydrochloride remaining. Upon reaction completion, the reaction was diluted with ethyl acetate (396 kg, 10 vol) and washed with sat. aqueous $NaHCO_3$ (2×92 kg). The aqueous layer was back extracted with ethyl acetate (198 kg, 5 vol) and the combined organic layers were dried with sodium sulfate. The drying agent was filtered away and the solution subjected to sequential solvent exchanges consisting of acetonitrile (2×139 kg) followed by ethyl acetate (4×238 kg) resulting in a slurry of DiNACMe in EtOAc. The material was filtered, washed with ethyl acetate and dried under vacuum to yield 45.05 kg (100%) of DiNACMe. A second run was performed as described to give 42.05 kg (100%) of DiNACMe.

Figure 12:
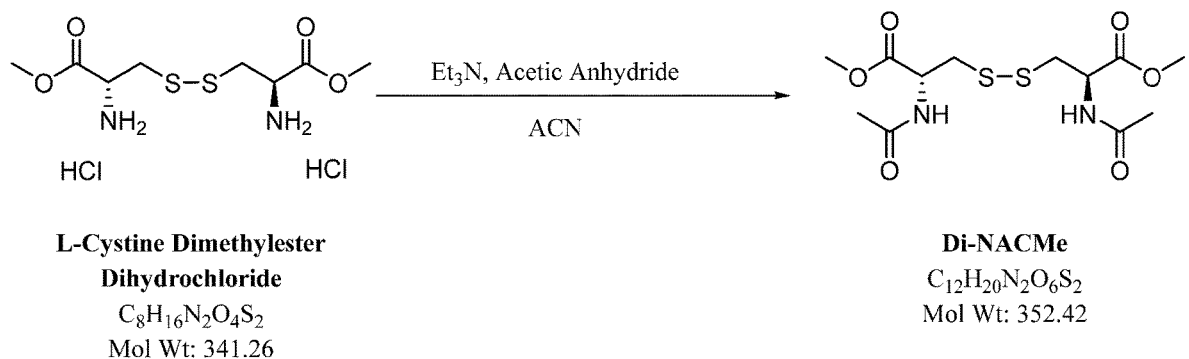
FIG. 12 shows step 2 in the formation of Di-NACMe.

FIG. 12 shows step 2 in the formation of Di-NACMe.

TABLE 3

| Reagents/Materials | MW | Eqs. | Moles | Density | Expected Amt (kg) |
|---|---|---|---|---|---|
| L-Cystine Dimethylester Dihydrchloride, ≥95% | 341.26 | 1.0 | 129 | — | 44 |
| Acetonitrile, ≥99% | 41.05 | 23 vol | — | 0.79 | 799 |
| Triethylamine (TEA), ≥99% | 101.19 | 4.2 | 544 | 0.73 | 55 |
| Acetic Anhydride, ≥99% | 102.09 | 2.1 | 274 | 1.08 | 28 |
| Sodium Bicarbonate, ≥99% (for 9%(w/w) $NaHCO_3$ (aq) soln) | 58.44 | 0.378 mass eq. | — | — | 18 |
| Process Water, Filtered (for Aqueous solution above) | 18.02 | — | — | 1.00 | 176 |
| Sodium Sulfate, anhydrous | 142.04 | — | — | — | * |
| Ethyl Acetate, ≥99% | 88.1 | 41 vol | — | 0.90 | 1625 |

TABLE 4

| Reference | 01NPI02-01 |
|---|---|

To clean 2000 L reactor charged
44 kg of L-Cystine Dimethylester Dihydrochloride (charged wet solids total weight charged 52.3 kg), and
799 kg of polish filtered Acetonitrile. Bubbled nitrogen into the contents of the reactor for 30 minutes and cooled the reactor to 0 ± 5° C. While maintaining the internal temperature <5° C. slowly, charged
55 kg of Triethylamine,
28 kg of Acetic Anhydride and allowed contents to agitate with an internal temperature of 0 ± 5° C. for 30 minutes. Reaction deemed complete by HPLC analysis.
Withdrew representative sample; submitted to QC laboratory for HPLC analysis.

TABLE 4-continued

| Reference | 01NPI02-01 | | | |
|---|---|---|---|---|

Step 2.32 - IPC for Reaction Completion
(L-Cystine Dimethylester Dihydrochloride ▶ Di-NACMe)

| 01NPI02 | L-Cystine Dimethylester Dihydrochloride | Di-NACMe | Reaction |
|---|---|---|---|
| –01-32 | 0.7% | 99.3% | Incomplete |
| –01-32-1 | 0.5% | 99.5% | Complete |
| –02-32 | 0.1% | 99.9% | Complete |

Charged
- 396 kg of filtered Ethyl Acetate and with agitation warmed the reactor contents to 20 ± 5° C. To the reactor charged
- 2 × 92 kg of 9% (w/w) Sodium Bicarbonate, aqueous solution, allowed phase separation each time. Dropped aqueous phase into clean HDPE drum labeled Step 2.39 - Aqueous Layer and Organic Layer into a clean drum labeled; Step 2.44-Di-NACMe in ACN/EtOAc.
- 198 kg To the reactor charged the contents of the drum labeled Step 2.39 - Aqueous Layer and
- 5.0 kg of filtered Ethyl Acetate allowed contents to agitate for 25 minutes. Allowed layers to separate, drained bottom layer into drum labeled; Step 2.48-Aqueous Layer and organic layer into clean drum labeled Step 2.44-Di-NACMe in ACN/EtOAc. To each drum (total 8) labeled Step 2.44-Di-NACMe in ACN/EtOAc charged
- 2 × 139 kg of Sodium Sulfate, anhydrous, agitated each drum with drum agitator for 5 minutes. To clean reactor charged, as room allowed, the contents of drums labeled Step 2.44 - Di-NACMe in ACN/EtOAc through a bag filter followed by a polish filter. Vacuum distilled the contents until all drums have been charged and rinsed. Continued distillation until 220 L remained in the reactor. Through a polish filter, charged of Acetonitrile and vacuum distilled until 220 L remained in the reactor. Withdrew representative sample; submitted to QC laboratory for GC analysis.

Step 2.72 - IPC for Residual Triethylamine by GC

| 01NPI02 | IPC Limit (ppm) | Actual Value (ppm) |
|---|---|---|
| –01-72 | Report >7020 | 158,244 |

Charged, through polish filter
- 4 × 238 kg of Ethyl Acetate, vacuum distilled until 220 L remained in the reactor. Agitated contents of the reactor with internal temperature of 0 ± 5° C. for 1 hour, filtered through Nutsche filter in two portions. Rinsed each portion with
- 79 kg of polish filtered Ethyl Acetate. Blown dry contents of the filter for at least 20 minutes with 10 ± 5 psig of nitrogen. Transferred wet (EtOAc) Di-NACMe filter cake into pre lined vacuum trays and dried to constant weight at ≤25° C. to afford 45.05 kg of dry Di-NACMe. Di-NACMe ready for processing in the next step. This procedure was repeated as 01NPI02-02.

Step 3 was performed by first sparging 28-30% ammonium hydroxide (244 kg, 8.44 eq) with nitrogen for 30 minutes. The solution was then cooled to 0±5° C. and 87.1 kg of DiNACMe added. The solution was stirred at 0±5° C. for 4 hours before sampling. The IPC showed 0.1% DiNACMe remaining and was deemed complete. The ammonium hydroxide was distilled to ~87 L and exchanged with degassed ethanol (3×344 kg) to a volume of ~87 L. Upon completion of the solvent exchanges, degassed ethanol (344 kg, 4 vol) was added and the slurry stirred for 1 hour at 0±5° C. The material was filtered, washed with degassed ethanol and dried under vacuum to yield 50.25 kg (63%) of diNACA.

Step 3A, the recrystallization of diNACA from water, was performed in a 200 L glass-lined reactor. Batch 01NPI03A-01 involved the recrystallization of 25.1 kg of diNACA from degassed water (151 kg, 6 vol) to yield 17.05 kg of diNACA. The remaining 25.1 kg of diNACA was recrystallized in batch 01NPI03A-02 to give 17.5 kg of diNACA. Both lots of recrystallized diNACA were combined (34.55 kg) and recrystallized a final time in batch 01NPI03A-03 to give 28.3 kg of purified diNACA.

Figure 13:
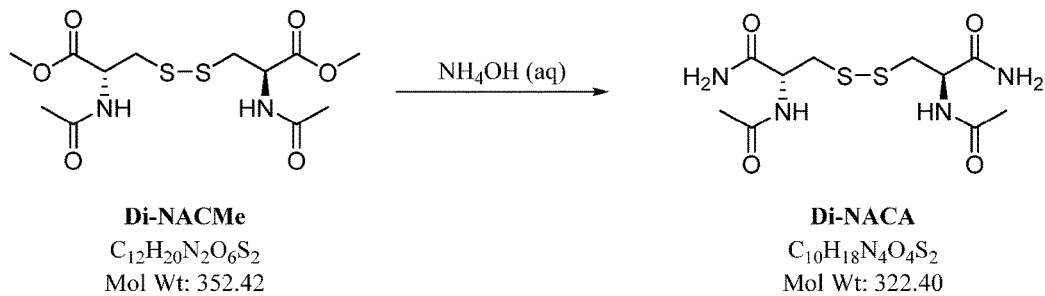
FIG. 13 shows step 3 the generation of diNACA.

FIG. 13 shows step 3 the generation of diNACA.

TABLE 5

| Reagents/Materials | MW | Eqs. | Moles | Density | Expected Amt (kg) |
|---|---|---|---|---|---|
| DiNACA | 352.42 | 1.0 | 247 | — | 87.1 |
| 28-30% Ammonium Hydroxide | 35.05 | 8.44 | 2088 | 0.9 | 244 |
| Ethanol, absolute 200 proof | 46.07 | 17 vol | — | 0.79 | 1170 |

TABLE 6

| Reference | 01NPI03-01 |
|---|---|
| 244 kg | To 2000 L Reactor charged, via diaphragm pump, of 28-30% Ammonium Hydroxide, with agitaion bubbled 3 ± 2 psig of nitrogen into the contents through the diptube for 30 minutes. Pressurized the reactor with 3 ± 2 psig of nitrogen and cooled the contents to 0 ± 5° C. Through solid shoot apparatus charged |
| 87.1 kg | of Di-NACMe and allowed contents to agitate with internal temperature of 0 ± 5° C. for 4 hours. Reaction deemed complete by HPLC analysis. Withdrew representative sample; submitted to QC laboratory for HPLC analysis. |

Step 3.28 - IPC for Reaction Completion (Di-NACMe ▶ DiNACA)

| 01NPI03 | Di-NACMe | DiNACA | Reaction |
|---|---|---|---|
| –01-28 | 0.1% | 99.9% | Complete |

| | |
|---|---|
| | Set the reactor jacket temperature for 15° C. and vacuum distilled the contents until ~87 L remained in the reactor not exceeding jacket temperature of 45° C. Charged through a polish filter |
| 3 × 344 kg | of degassed Ethanol, Absolute, 200 Proof and distilled the contents each time until ~87 L remained in the reactor. Charged through a polish filter |
| 344 kg | of degassed Ethanol, Absolute, 200 Proof, cooled reactor contents to 0 ± 5° C. and agitated for 1 hour with in internal temperature of 0 ± 5° C. Verified the reactor contained a thick, filterable slurry of solids. Reactor contents were filtered in two portions through Nutsche filter, rinsed each portion with |
| 69 kg | of degassed Ethanol, Absolute, 200 Proof and blown filter contents dry for at least 20 minutes with 10 ± 5 psig of nitrogen. Transferred wet - DiNACA filter cake into pre lined vacuum trays and dried to constant weight at ≤45° C. to afford total of 50.52 kg of DiNACA. DiNACA ready for processing in the next step. |

Figure 14:
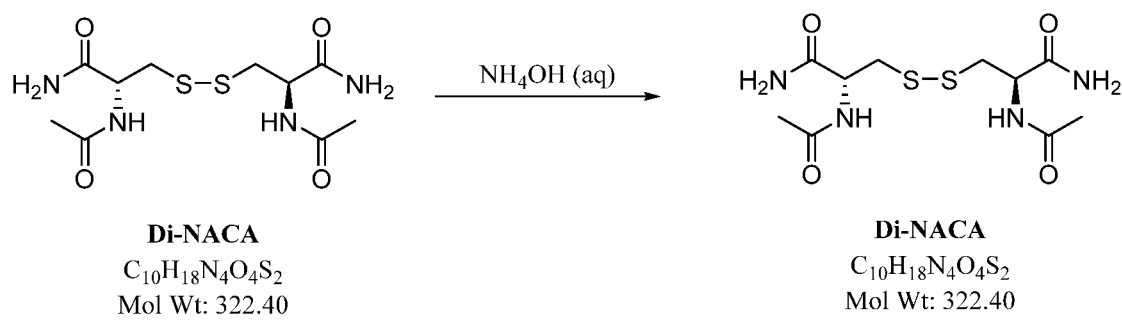
FIG. 14 shows step 3a the purification of DiNACA.

FIG. 14 shows step 3A the purification of DiNACA.

TABLE 7

| Reagents/Materials | MW | Eqs. | Moles | Density | Expected Amt (kg) |
|---|---|---|---|---|---|
| DiNACA | 322.40 | 1.0 | 77.9 | — | 25.1 |
| Process Water, Filtered | 18.02 | 8 vol | — | 1.0 | 201 |

TABLE 8

| Reference | 01NPI03A-01 |
|---|---|
| | To 2000 L Reactor charged |
| 151 kg | of Process Water, Filtered. Reactor contents were agitated degassed for at least 30 minutes. While maintaining nitrogen blanket charged to the reactor |
| 25.1 kg | of DiNACA, heated contents to reflux (~100° C.) and agitated at reflux until complete solution was obtained. Once complete solution obtained, cooled the reactor contents to 20 ± 5° C. Reactor contents were agitated at 20 ± 5° C. for at 3 hours, filtered via Nutsche Filter, rinsed with |
| 50.0 kg | of degassed Process Water, Filtered. Transferred wet-DiNACA filter cake into pre lined vacuum trays and dried to constant weight at ≤45° C. to afford total of 17.05 kg of DiNACA. DiNACA ready for processing in the next step. This procedure was repeted as 01NPI03A-02 and 01NPI03A-03. |

FIG. 1 is an X-Ray Powder Diffractogram for (2R,2R')-3,3'-disulfanediyl bis(2-acetamidopropanamide) of the present invention.

Figure 2:
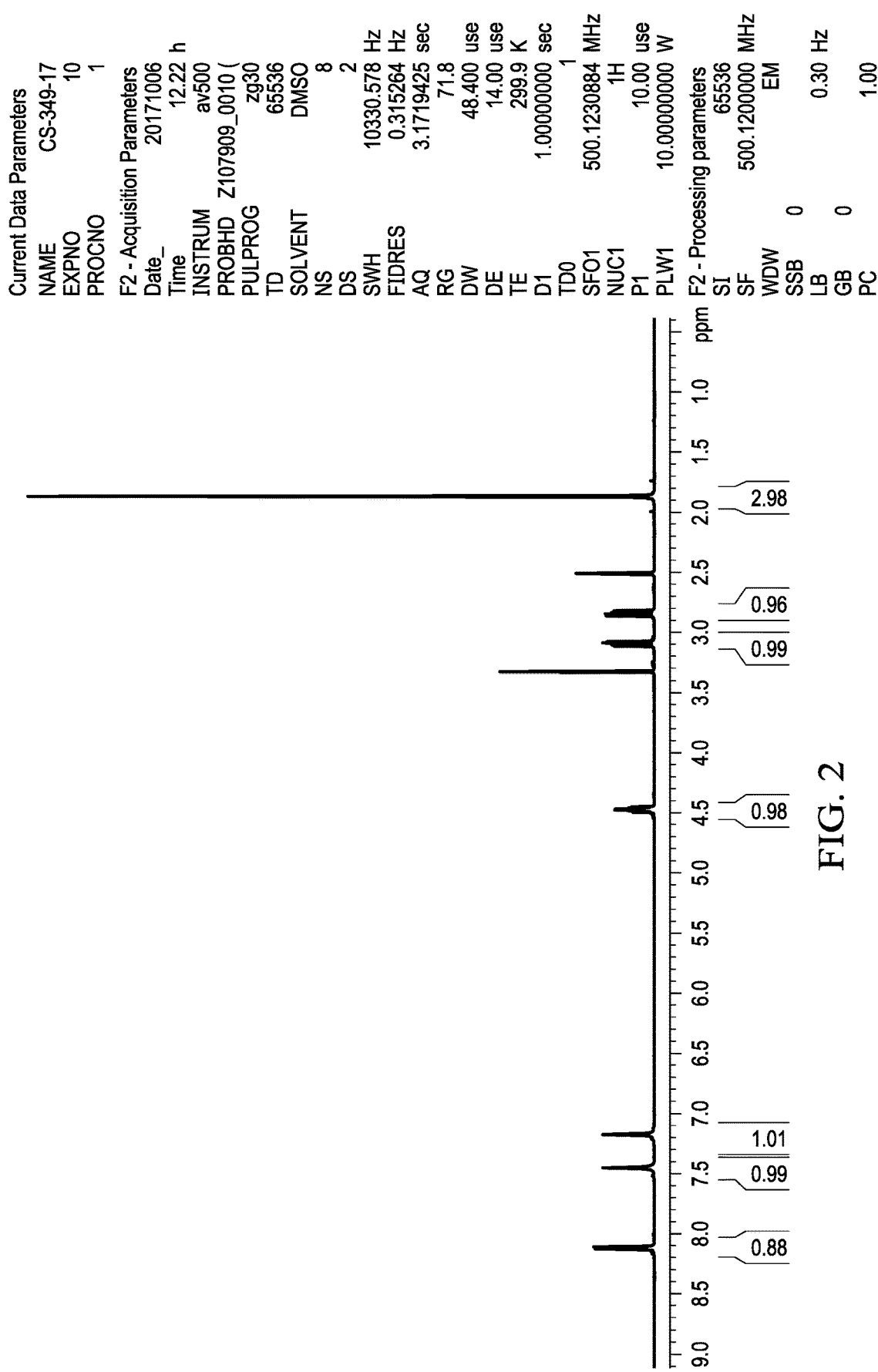
FIG. 2 shows proton nuclear magnetic spectrum for (2R,2R')-3,3'-disulfanediyl bis(2-acetamidopropanamide) of the present invention.

FIG. 2 shows proton nuclear magnetic spectrum for (2R,2R')-3,3'-disulfanediyl bis(2-acetamidopropanamide) of the present invention.

Figure 3:
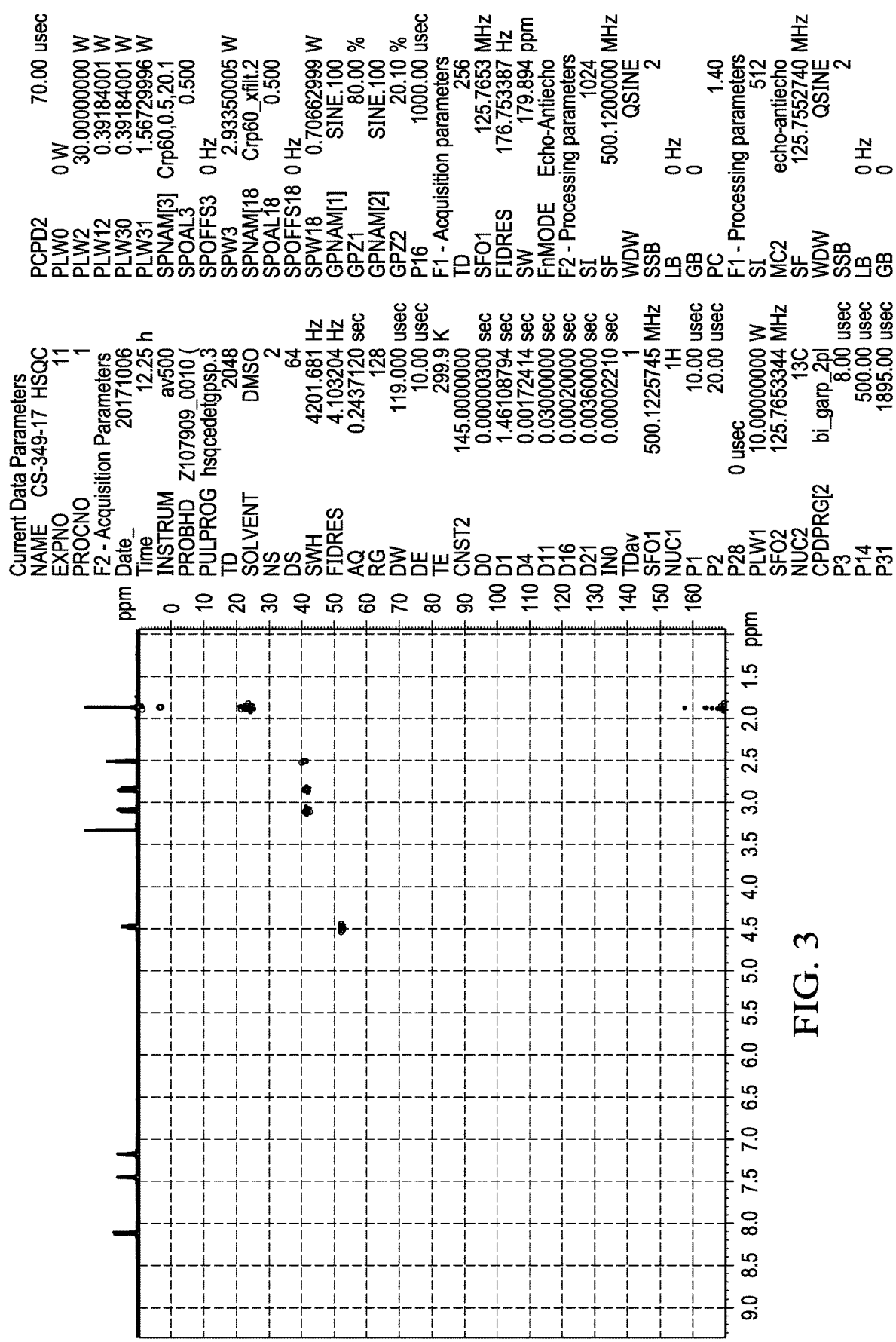
FIG. 3 shows heteronuclear single quantum correlation spectrum for (2R,2R')-3,3'-disulfanediyl bis(2-acetamidopropanamide) of the present invention.

FIG. 3 shows heteronuclear single quantum correlation spectrum for (2R,2R')-3,3'-disulfanediyl bis(2-acetamidopropanamide) of the present invention.

Figure 4:
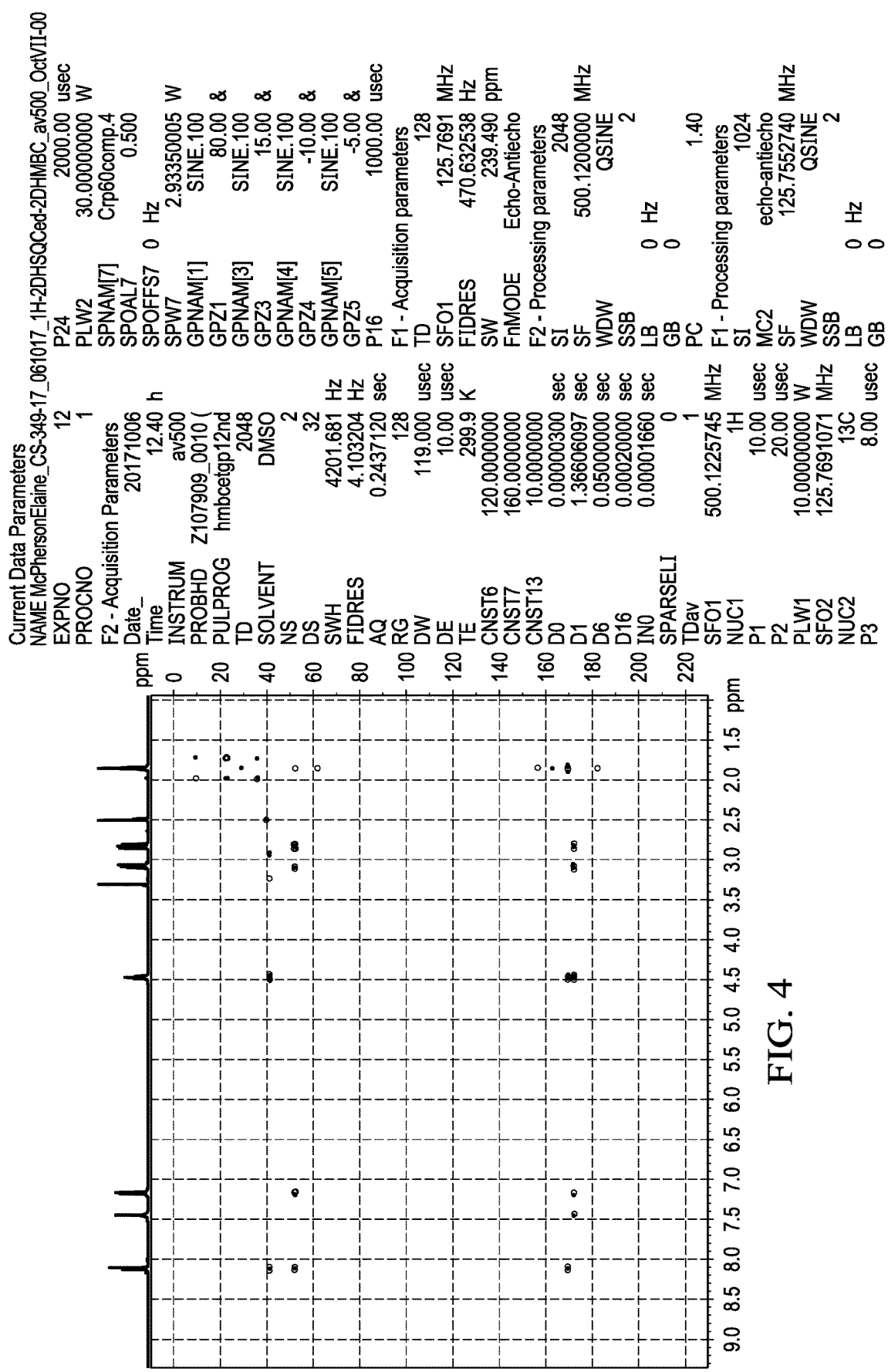
FIG. 4 shows heteronuclear multiple-bond correlation spectrum for (2R,2R')-3,3'-disulfanediyl bis(2-acetamidopropanamide) of the present invention.

FIG. 4 shows heteronuclear multiple-bond correlation spectrum for (2R,2R')-3,3'-disulfanediyl bis(2-acetamidopropanamide) of the present invention.

Figure 5:
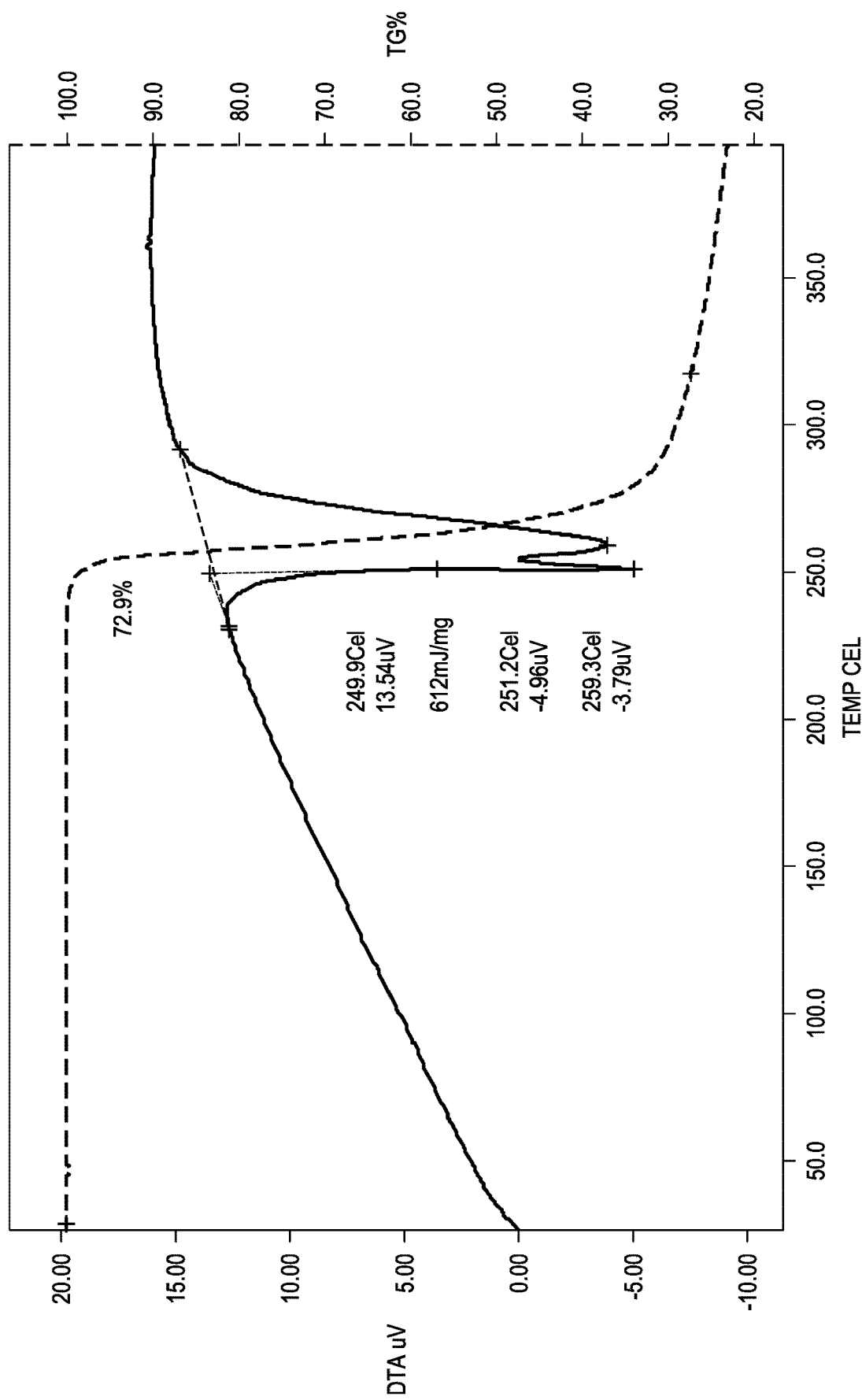
FIG. 5 shows a combination thermogravimetric and differential thermal analysis for (2R,2R')-3,3'-disulfanediyl bis (2-acetamidopropanamide) of the present invention.

FIG. 5 shows a combination thermogravimetric and differential thermal analysis for (2R,2R')-3,3'-disulfanediyl bis (2-acetamidopropanamide) of the present invention.

Figure 6:
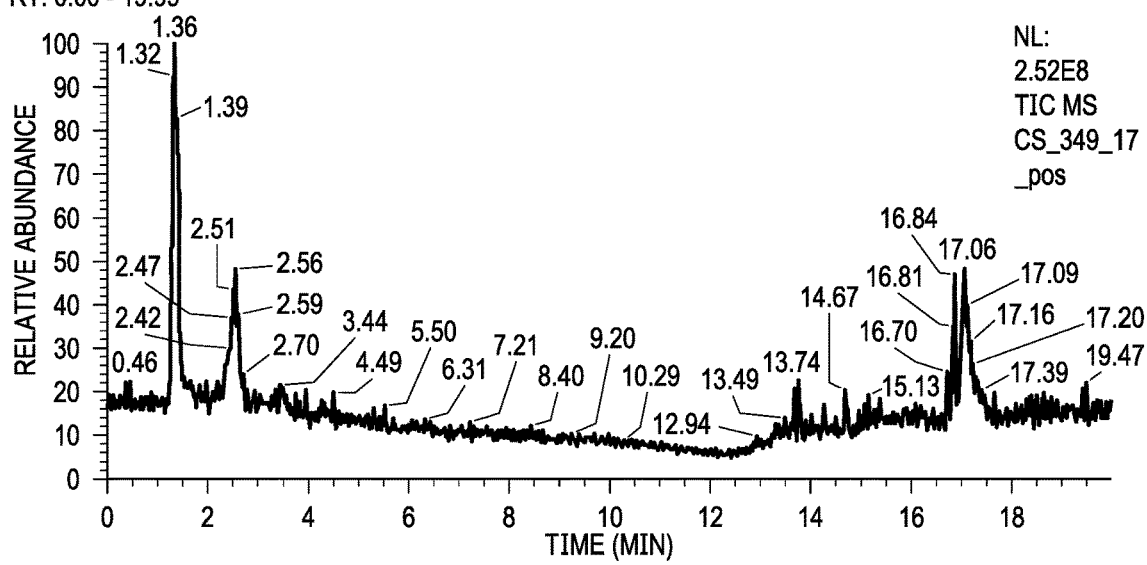
FIG. 6 shows liquid chromatographic mass spectrometric data for (2R,2R')-3,3'-disulfanediyl bis(2-acetamidopropanamide) of the present invention.
Figure 6:
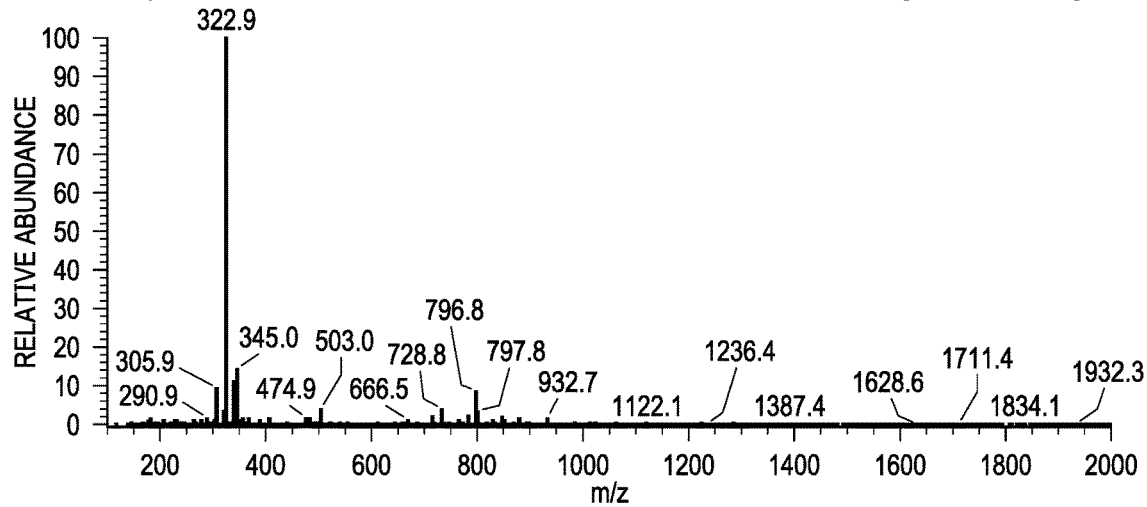
Figure 6:
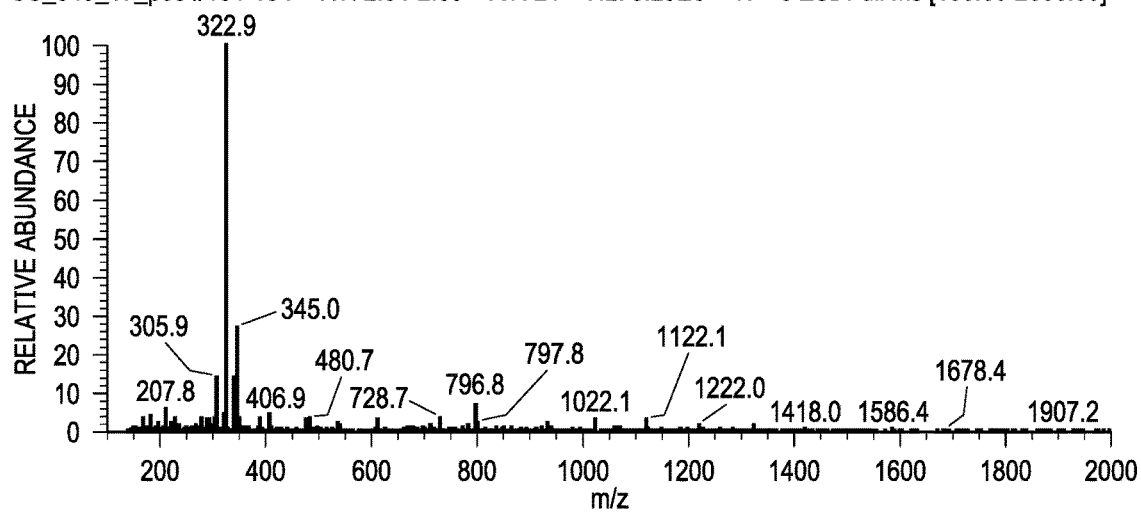

FIG. 6 shows liquid chromatographic mass spectrometric data for (2R,2R')-3,3'-disulfanediyl bis(2-acetamidopropanamide) of the present invention.

Example 1

Ophthalmic Suspension.

Sodium phosphate, propylene glycol, Pluronic F127, edetate disodium benzalkonium chloride are dissolved in 800 ml of water. The pH is adjusted with dilute HCl or NaOH. DiNACA is added. The osmolarity is within 250 to 350 mOsm Kg. Solution is q.s. with water to a total of 1 liter. The formulation is sterilized by autoclave. This is only one ophthalmic formulation and does not exclude other solution formulations.

TABLE 9

| Component | Quantity |
|---|---|
| diNACA | 1 g to 100 g |
| Sodium phosphate | 0.8 g |
| Propylene glycol | 18 g |
| Pluronic F127 | 50 g |
| Edetate disodium | 0.1 g |
| Benzalkonium chloride | 0.1 g |
| 0.1N HCl or NaOH | Adjust pH to 7.4 |
| Water for Injection | Q.S. 1000 ml |

Compounds described herein can be provided in isolated or purified form. Isolated or purified compounds are a group of compounds that have been separated from their environment, such as from a crude reaction mixture if made in a laboratory setting or removed from their natural environment if naturally occurring. Examples of the purity of the isolated compound include, for example, at least 50%, 55%, 60%, 65%, 70%, 75%, 80%, 85%, 90%, 95%, to 100% by weight.

Another aspect of the invention provides a unit quantum of a compound described herein, such as an amount of at least (a) one microgram of a disclosed compound, (b) one mg, or (c) one gram. In further embodiments, the quantum is, for example, at least 0.01, 0.02, 0.03, 0.04, 0.05, 0.1, 0.2, 0.3, 0.4, 0.5, or 1 mole of the compound. The present amounts also cover lab-scale (e.g., gram scale including 1, 2, 3, 4, 5 g, etc.), kilo-lab scale (e.g., kilogram scale including 1, 2, 3, 4, 5 kg, etc.), and industrial or commercial scale (e.g., multi-kilogram or above scale including 100, 200, 300, 400, 500 kg, etc.) quantities as these will be more useful in the actual manufacture of a pharmaceutical. Industrial/commercial scale refers to the amount of product that would be produced in a batch that was designed for clinical testing, formulation, sale/distribution to the public, etc.

Doses of a compound provided herein, or a pharmaceutically acceptable salt thereof, vary depending on factors such as: specific indication to be treated; age and condition of a patient; and amount of a second active agent used, if any. Generally, a compound provided herein, or a pharmaceutically acceptable salt thereof, may be used in an amount of from about 0.1 mg to about 1 g per day, or from about 0.1 mg to about 500 mg per day, and can be adjusted in a conventional fashion (e.g., the same amount administered each day of the treatment), in cycles (e.g., one week on, one week off), or in an amount that increases or decreases over the course of treatment. In other embodiments, the dose can be from about 1 mg to 1000 mg, from about 1 mg to about 450 mg, from about 0.1 mg to about 150 mg, from about 1 mg to about 300 mg, from about 10 mg to about 100 mg, from about 0.1 mg to about 50 mg, from about 1 mg to about 50 mg, from about 10 mg to about 50 mg, from about 20 mg to about 30 mg, or from about 1 mg to about 20 mg. In yet other embodiments, the daily dose can be from about 50 mg to 75 mg, 75 mg to 100 mg, 100 mg to 125 mg, 125 mg to 150 mg, 150 mg to 175 mg, 175 mg to 200 mg, 200 mg to 225 mg, 225 mg to 250 mg, 250 mg to 275 mg, 275 mg to 300 mg, 300 mg to 325 mg, 325 mg to 350 mg, 350 mg to 375 mg, 375 mg to 400 mg, 400 mg to 425 mg, or 425 mg to 450 mg. In certain embodiments, (2R,2R')-3,3'-disulfanediyl bis(2-acetamidopropanamide) is administered at a daily dosage in the range of about 125 mg to 150 mg, 150 mg to 175 mg, 175 mg to 200 mg, 200 mg to 225 mg, 225 mg to 250 mg, 250 mg to 275 mg, or 275 mg to 300 mg. In certain embodiments, (2R,2R')-3,3'-disulfanediyl bis(2-acetamidopropanamide) is administered at a daily dosage in the range of about 50 mg to 75 mg, 75 mg to 100 mg, 100 mg to 125 mg, 125 mg to 150 mg, 150 mg to 175 mg, 175 mg to 200 mg, 200 mg to 225 mg, 225 mg to 250 mg, 250 mg to 275 mg, or 275 mg to 300 mg. In certain embodiments, (2R,2R')-3,3'-disulfanediyl bis(2-acetamidopropanamide) is administered at a daily dosage in the range of about 125 mg to 150 mg or 150 mg to 175 mg. In certain embodiments, (2R,2R')-3,3'-disulfanediyl bis(2-acetamidopropanamide) is administered at a daily dosage in the range of about 125 mg to 175 mg. In certain embodiments, (2R,2R')-3,3'-disulfanediyl bis(2-acetamidopropanamide) is administered at a daily dosage in the range of about 140 mg to 160 mg. In yet other embodiments, (2R,2R')-3,3'-disulfanediyl bis(2-acetamidopropanamide) is administered at a daily dosage in the range of about 50 mg to 175 mg, or about 125 mg to 175 mg. In yet other embodiments, the daily dose is less than about 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 425 mg, or 450 mg. In yet other embodiments, the daily dose is less than about 125 mg, 150 mg, or 175 mg. The formulation may also exclude non-active ingredients, in which case the formulation will "consist essentially" of the active agents claimed herein, as non-active ingredients. The formulation may also exclude all other ingredients, in which case the formulation will "consist" of the active agents. Each of these variants are contemplated herein.

Example 2

Preparation of NACA-d$_3$. A process for preparing 10 mg of D$_3$-N-acetyl cysteine amide 5 (NACA-d$_3$) is described. The inventors used various approaches to make D$_3$-N-acetyl cysteine amide by using the chemistry shown in Scheme 1. In each case, the inventors observed a mixture of compounds while forming the methyl ester 3 and LCMS suggests that several other compounds were made, including 4 in addition to the desired 3. Treatment of this mixture with ammonium hydroxide gave 6, with no observation of the desired 5 by LCMS.

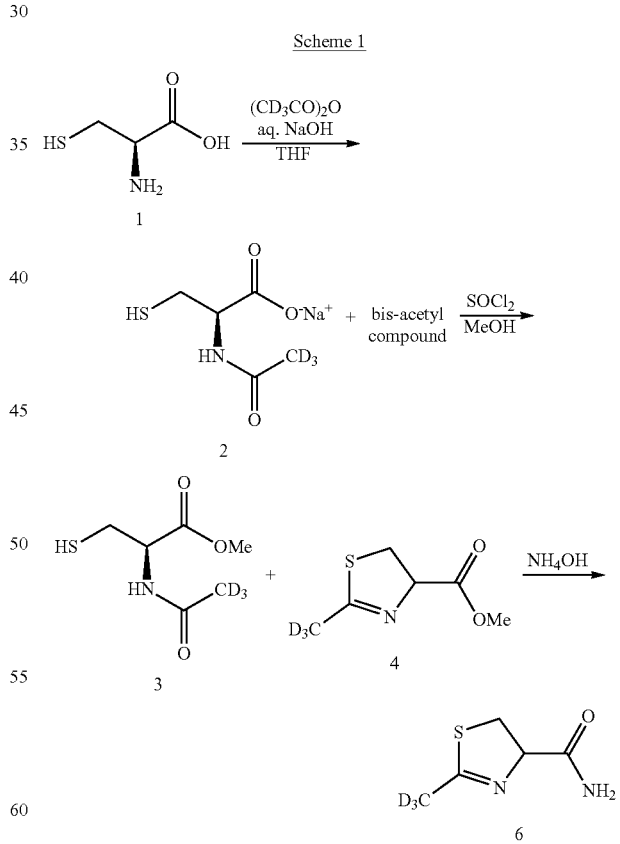

Cysteine methyl ester 7 (Scheme 2) allows the elimination of the problematic transformation of 2 to 3. Acetylation affords 3 directly from 7 and then reaction with ammonium hydroxide provides the target compound 5.

Scheme 2

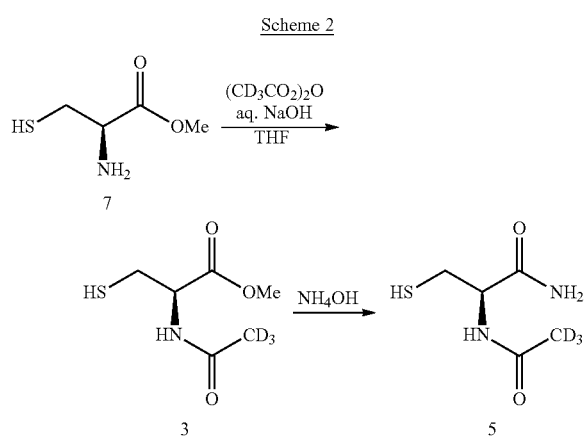

TABLE 10

| Reaction | Notebook | Scale (g) | Yield (%) | Comments |
|---|---|---|---|---|
| 1 to 2 | 1719-TTP-2 | 0.50 | N/A | 2 eq. of NaOH, 1 eq. anhydride. LCMS shows a mixture of 2 and bis-acetyl. |
| 2 to 3 | 1719-TTP-3 | 0.78 | N/A | LCMS shows a mixture of 3 and 4. |
| 3 to 5 | 1719-TTP-4 | 0.38 | N/A | LCMS shows a mass for 6. |
| 1 to 2 | 1719-TTP-5 | 0.50 | N/A | 3 eq. NaOH, 2 eq. anhydride. Clean bis-acetyl by crude $^1$H NMR. |
| 2 to 3 | 1719-TTP-6 | 0.96 | N/A | LCMS shows a mixture of 3 and 4. |
| 3 to 5 | 1719-TTP-7 | 0.23 | N/A | LCMS shows a mass for 6. |
| 1 to 2 | 1719-TTP-8 | 0.50 | N/A | With 3.0 equiv NaOH and 2.0 equiv. anhydride. Clean bis-acetyl by crude $^1$H NMR. |

| Reaction | Notebook | Scale (g) | Yield (%) | Comments |
|---|---|---|---|---|
| 2 to 3 | 1719-TTP-9 | 0.96 | NA | Carefully monitored by LC-MS. Formation of 4 is competitive with 3. |
| 3 to 5 | 1719-TTP-10 | 0.93 | NA | LCMS shows mass for 6. |
| 1 to 2 | 1719-TTP-11 | 0.50 | NA | Precisely 2.0 eq. of NaOH, 1.0 eq. anhydride. LCMS shows a mixture of 2 and bis-acetyl. Underway. |

TABLE 11

N-2-acetyl-L-cysteineamide-d$_3$

| Test | Acceptance Criteria | Result |
|---|---|---|
| Appearance | Report Only | White crystalline solid |
| Purity | 95% or better | >95% by NMR |
| $^1$H NMR Spectrum (DMSO-d$_6$) | Consistent with structure | Consistent with structure[1] |
| Mass Spectrum | Consistent with structure | Consistent with structure[2] |
| Isotopic Abundance | 97% or better D$_3$ with no detectable D$_0$ | No D$_2$, D$_1$ or D$_0$ detected by NMR.[3] |

[1]$^1$H NMR spectrum also shows 1.52% w/w water, and 0.28% w/w ethanol. No visible acetate protons.
[2]MS (ESI+) for C$_5$H$_7$D$_3$N$_2$O$_2$S m/z 188.0 (M + Na)$^+$ MS (ESI−) for C$_5$H$_7$D$_3$N$_2$O$_2$S m/z 164.0 (M − H)$^−$.
[3]Mass peaks are visible at 185.0 (ESI$^+$) and 162.0 (ESI$^−$) but we do not believe these are due to D$_0$ or D$_1$ species, respectively.

Figure 7:
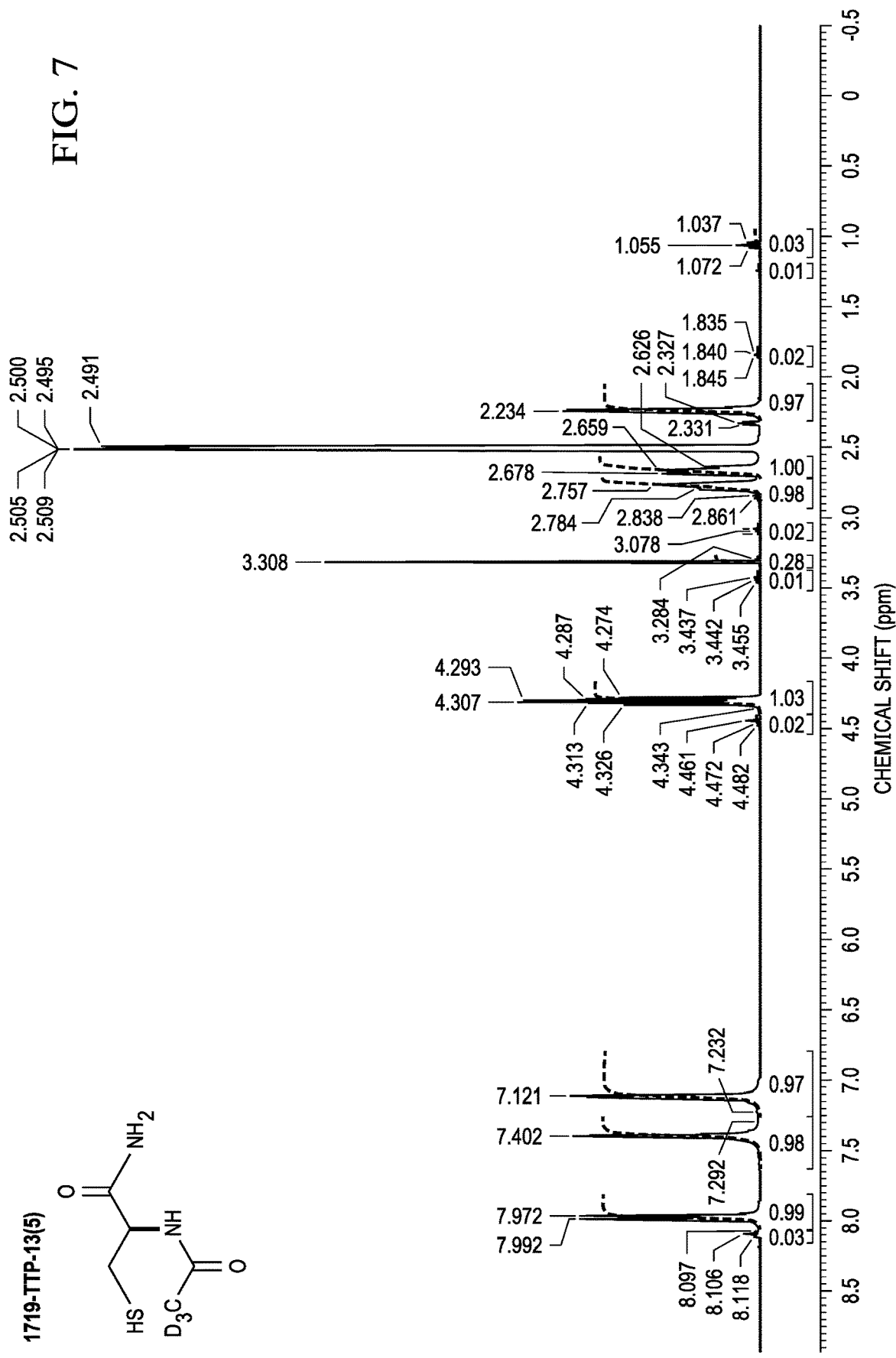
FIG. 7 shows chemical shift data for one batch of the N-2-acetyl-L-cysteineamide-$d_3$ (NACA-$d_3$) of the present invention.

FIG. 7 shows chemical shift data for one batch of the N-2-acetyl-L-cysteineamide-d$_3$ of the present invention.

Figure 8:
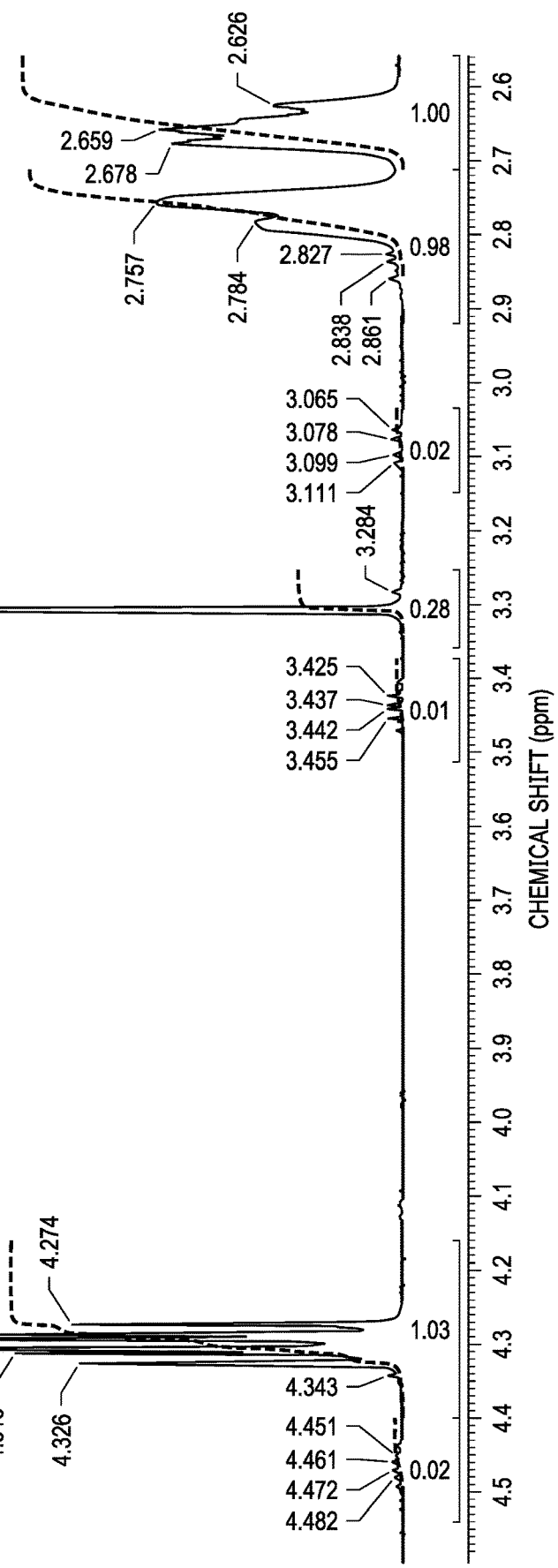
FIG. 8 shows additional chemical shift data for another batch of the N-2-acetyl-L-cysteineamide-$d_3$ of the present invention.
Figure 8:
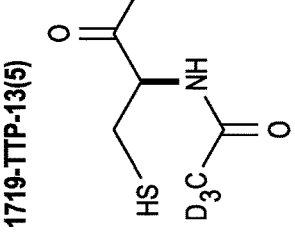

FIG. 8 shows chemical shift data for another batch of the N-2-acetyl-L-cysteineamide-d$_3$ of the present invention.

Figure 9:
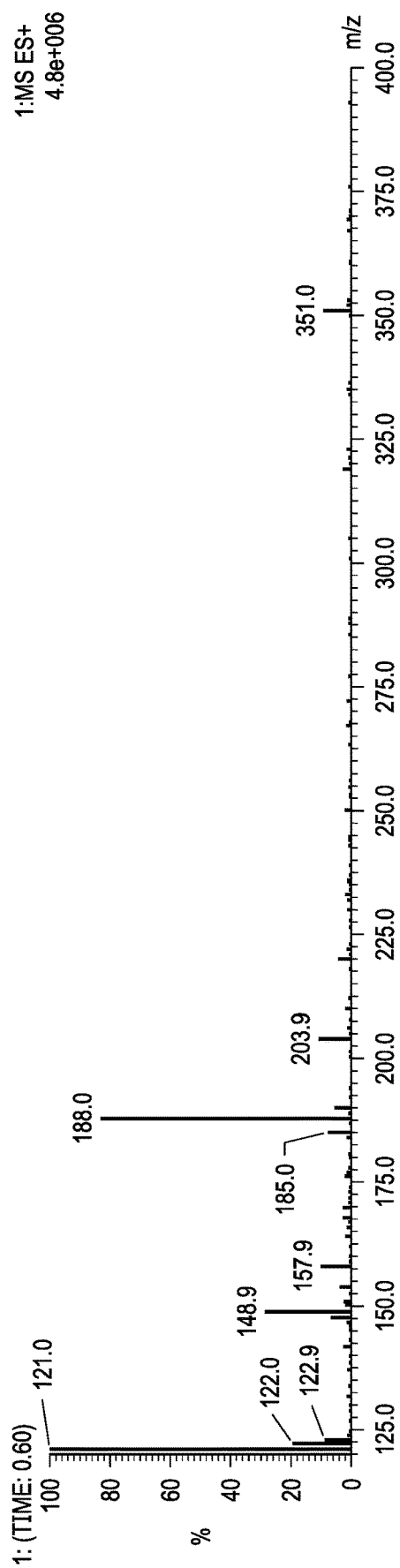
FIG. 9 shows MS results the N-2-acetyl-L-cysteineamide-$d_3$ of the present invention.

FIG. 9 shows MS results the N-2-acetyl-L-cysteineamide-d$_3$ of the present invention.

Figure 10:
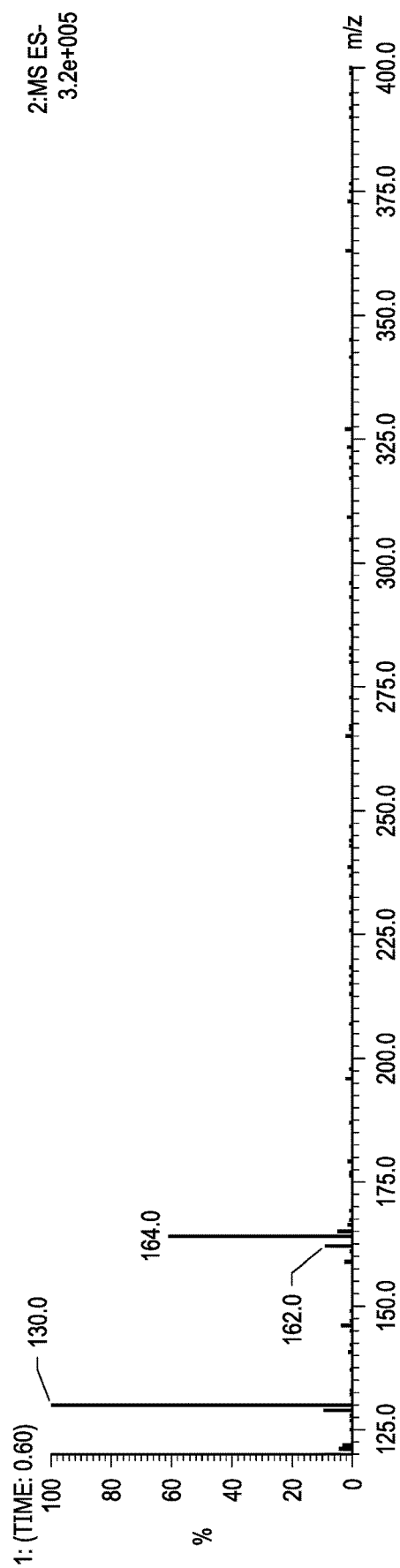
FIG. 10 shows additional MS results the N-2-acetyl-L-cysteineamide-$d_3$ of the present invention.

FIG. 10 shows MS results the N-2-acetyl-L-cysteineamide-d$_3$ of the present invention.

Example. Oral Formulation. NACA-d$_3$ is dissolved in a mixture of water and Ora-Sweet®. Ora-Sweet is a commercially available syrup vehicle containing water, sucrose, glycerin, sorbitol, flavoring, buffering agents (citric acid and/or sodium phosphate), methyl paraben and potassium sorbate, pH 4.2 manufactured by Paddock Laboratories, Inc., Minneapolis, Minn. ORA-SWEET has a cherry syrup flavor. Neat NACA-d3 has a mild sulfur odor. When mixed with ORA-SWEET there is no odor and the taste is that of ORA-SWEET only. ORA-SWEET is a pale pink clear solution. The lowest concentration of NACA-d3 (250 mg/100l ORA-SWEET) is a pale pink clear solution while the highest concentration of NACA-d3 (4,000 mg/100 ml ORA-SWEET) is a very pale pink clear solution.

Instructions for Preparation of NACA-d$_3$ Oral Solution:
1. Weigh NACA-d$_3$ [either 250, 750, 1500, 3000 or 4000 mg (±1 mg), as appropriate for the particular dose group] and place into a 125 mL (approximately) capacity opaque high density polyethylene, labeled bottle with opaque polypropylene screw cap.
2. Measure 50 mL of Purified Water and pour into each bottle containing NACA-d$_3$ and shake vigorously by hand (at least 30 seconds) to dissolve.
3. Measure 50 mL Ora-Sweet and pour into each bottle containing NACA-d$_3$.
   a. Shake vigorously by hand (at least 30 seconds) to dissolve.
   b. This solution may be stored for up to 8 hours at room temperature (20° C. 5° C.), protected from light. (If solution is not consumed after these storage conditions, do not use, i.e., dispose and document.
4. Immediately prior to dosing, shake well for 10 seconds.
5. Provide to subject.
6. Have subject drink total contents of bottle.
7. Pour another 20 ml of Ora-Sweet into bottle, cap and shake vigorously for 5 seconds (this is "rinse #1)
8. Have subject drink total contents of bottle.
9. Pour another 20 ml of Ora-Sweet into bottle, cap and shake vigorously for 5 seconds (this is "rinse #2).

Have subject drink total contents of bottle (resulting in an approximately total volume of 140 ml Ora-Sweet mixture consumed by each subject for each dose regimen).

Example 2. NACA-d$_3$ Ophthalmic Solution

Sodium phosphate, propylene glycol, Pluronic F127, edetate disodium benzalkonium chloride are dissolved in 800 ml of water. The pH is adjusted with dilute HCl or NaOH. NACA-d$_3$ is added. The osmolarity is within 250 to 350 mOsm Kg. Solution is q.s. with water to a total of 1 liter. The formulation is sterilized by autoclave. This is only one ophthalmic formulation and does not exclude other solution formulations.

TABLE 12

| Component | Quantity |
|---|---|
| NACA-d$_3$ | 1 g to 100 g |
| Sodium phosphate | 0.8 g |
| Propylene glycol | 18 g |
| Pluronic F127 | 50 g |

TABLE 12-continued

| Component | Quantity |
|---|---|
| Edetate disodium | 0.1 g |
| Benzalkonium chloride | 0.1 g |
| 0.1N HCl or NaOH | Adjust pH to 7.4 |
| Water for Injection | Q.S. 1000 ml |

Compounds described herein can be provided in isolated or purified form. Isolated or purified compounds are a group of compounds that have been separated from their environment, such as from a crude reaction mixture if made in a laboratory setting or removed from their natural environment if naturally occurring. Examples of the purity of the isolated compound include, for example, at least 50%, 55%, 60%, 65%, 70%, 75%, 80%, 85%, 90%, 95%, 96%, 97%, 98%, 99%, or 100% by weight.

Another aspect of the invention provides a unit quantum of a deuterium-enriched compound described herein, such as an amount of at least (a) one microgram of a disclosed deuterium-enriched compound, (b) one mg, or (c) one gram. In further embodiments, the quantum is, for example, at least 0.01, 0.02, 0.03, 0.04, 0.05, 0.1, 0.2, 0.3, 0.4, 0.5, or 1 mole of the compound. The present amounts also cover lab-scale (e.g., gram scale including 1, 2, 3, 4, 5 g, etc.), kilo-lab scale (e.g., kilogram scale including 1, 2, 3, 4, 5 kg, etc.), and industrial or commercial scale (e.g., multi-kilogram or above scale including 100, 200, 300, 400, 500 kg, etc.) quantities as these will be more useful in the actual manufacture of a pharmaceutical. Industrial/commercial scale refers to the amount of product that would be produced in a batch that was designed for clinical testing, formulation, sale/distribution to the public, etc.

Doses of a compound provided herein, or a pharmaceutically acceptable salt thereof, vary depending on factors such as: specific indication to be treated; age and condition of a patient; and amount of a second active agent used, if any. Generally, a compound provided herein, or a pharmaceutically acceptable salt thereof, may be used in an amount of from about 0.1 mg to about 1 g per day, or from about 0.1 mg to about 500 mg per day, and can be adjusted in a conventional fashion (e.g., the same amount administered each day of the treatment), in cycles (e.g., one week on, one week off), or in an amount that increases or decreases over the course of treatment. In other embodiments, the dose can be from about 1 mg to 1000 mg, from about 1 mg to about 450 mg, from about 0.1 mg to about 150 mg, from about 1 mg to about 300 mg, from about 10 mg to about 100 mg, from about 0.1 mg to about 50 mg, from about 1 mg to about 50 mg, from about 10 mg to about 50 mg, from about 20 mg to about 30 mg, or from about 1 mg to about 20 mg. In yet other embodiments, the daily dose can be from about 50 mg to 75 mg, 75 mg to 100 mg, 100 mg to 125 mg, 125 mg to 150 mg, 150 mg to 175 mg, 175 mg to 200 mg, 200 mg to 225 mg, 225 mg to 250 mg, 250 mg to 275 mg, 275 mg to 300 mg, 300 mg to 325 mg, 325 mg to 350 mg, 350 mg to 375 mg, 375 mg to 400 mg, 400 mg to 425 mg, or 425 mg to 450 mg. In certain embodiments, the deuterium-enriched $D_3$-N-acetyl cysteine amide is administered at a daily dosage in the range of about 125 mg to 150 mg, 150 mg to 175 mg, 175 mg to 200 mg, 200 mg to 225 mg, 225 mg to 250 mg, 250 mg to 275 mg, or 275 mg to 300 mg. In certain embodiments, the deuterium-enriched $D_3$-N-acetyl cysteine amide is administered at a daily dosage in the range of about 50 mg to 75 mg, 75 mg to 100 mg, 100 mg to 125 mg, 125 mg to 150 mg, 150 mg to 175 mg, 175 mg to 200 mg, 200 mg to 225 mg, 225 mg to 250 mg, 250 mg to 275 mg, or 275 mg to 300 mg. In certain embodiments, the deuterium-enriched $D_3$-N-acetyl cysteine amide is administered at a daily dosage in the range of about 125 mg to 150 mg or 150 mg to 175 mg. In certain embodiments, the deuterium-enriched $D_3$-N-acetyl cysteine amide is administered at a daily dosage in the range of about 125 mg to 175 mg. In certain embodiments, the deuterium-enriched $D_3$-N-acetyl cysteine amide is administered at a daily dosage in the range of about 140 mg to 160 mg. In yet other embodiments, the $D_3$-N-acetyl cysteine amide-enriched $D_3$-N-acetyl cysteine amide is administered at a daily dosage in the range of about 50 mg to 175 mg, or about 125 mg to 175 mg. In yet other embodiments, the daily dose is less than about 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 425 mg, or 450 mg. In yet other embodiments, the daily dose is less than about 125 mg, 150 mg, or 175 mg. The formulation may also exclude non-active ingredients, in which case the formulation will "consist essentially" of the active agents claimed herein, as non-active ingredients. The formulation may also exclude all other ingredients, in which case the formulation will "consist" of the active agents. Each of these variants are contemplated herein.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), property(ies), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skill in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

To aid the Patent Office, and any readers of any patent issued on this application in interpreting the claims appended hereto, applicants wish to note that they do not intend any of the appended claims to invoke paragraph 6 of 35 U.S.C. § 112 as it exists on the date of filing hereof unless the words "means for" or "step for" are explicitly used in the particular claim.

For each of the claims, each dependent claim can depend both from the independent claim and from each of the prior dependent claims for each and every claim so long as the prior claim provides a proper antecedent basis for a claim term or element.

What is claimed is:

1. A method of treating a disease associated with oxidative damage, comprising administering a pharmaceutical composition comprising an enantiopure (2R,2R')-3,3'-disulfanediyl bis(2-acetamidopropanamide)(diNACA) with at least 99% purity to a patient in need thereof.

2. The method of claim 1, wherein the disease is an eye disease or disorder.

3. The method of claim 1, wherein the disease is retinitis pigmentosa.

4. The method of claim 1, wherein the disease is beta-thallassemia, cataracts, chronic obstructive pulmonary disease, macular degeneration, contrast-induced nephropathy, asthma, lung contusion, methamphetamine-induced oxidative stress, multiple sclerosis, Parkinson's disease, platelet apoptosis, Tardive dyskinesia, Alzheimer disease, HIV-1-associated dementia, mitochondrial diseases, myocardial myopathy, neurodegenerative diseases, pulmonary fibrosis, skin pigmentation, skin in need of rejuvenation, antimicrobial infection, or Friedreich's ataxia.

5. The method of claim 1, wherein a dose of the diNACA is from about 1 mg to 1000 mg, from about 1 mg to about 450 mg, from about 0.1 mg to about 150 mg, from about 1 mg to about 300 mg, from about 10 mg to about 100 mg, from about 0.1 mg to about 50 mg, from about 1 mg to about 50 mg, from about 10 mg to about 50 mg, from about 20 mg to about 30 mg, or from about 1 mg to about 20 mg.

6. A method of treating a disease associated with oxidative damage, comprising administering a pharmaceutical composition comprising an enantiopure (2R,2R')-3,3'-disulfanediyl bis(2-acetamidopropanamide) with at least 99% purity to a patient in need thereof.

7. The method of claim 6, wherein the disease is an eye disease or disorder, retinitis pigmentosa, cataracts, chronic obstructive pulmonary disease, neurodegenerative diseases, pulmonary fibrosis, skin pigmentation, skin in need of rejuventation, or Friedreich's ataxia.

* * * * *